(12) United States Patent
Bergeron, Jr.

(10) Patent No.: US 11,931,346 B2
(45) Date of Patent: Mar. 19, 2024

(54) USES OF 4'-DESFERRITHIOCIN ANALOGS

(71) Applicant: University of Florida Research Foundation, Incorporated, Gainesville, FL (US)

(72) Inventor: Raymond J. Bergeron, Jr., Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 10 days.

(21) Appl. No.: 17/321,210

(22) Filed: May 14, 2021

(65) Prior Publication Data

US 2022/0105078 A1 Apr. 7, 2022

Related U.S. Application Data

(60) Continuation of application No. 15/424,557, filed on Feb. 3, 2017, now abandoned, which is a division of application No. 14/363,886, filed as application No. PCT/US2012/069795 on Dec. 14, 2012, now abandoned.

(60) Provisional application No. 61/576,920, filed on Dec. 16, 2011.

(51) Int. Cl.
A61K 31/426 (2006.01)
C07D 277/10 (2006.01)

(52) U.S. Cl.
CPC .......... *A61K 31/426* (2013.01); *C07D 277/10* (2013.01)

(58) Field of Classification Search
CPC .............................. A61K 31/426; C07D 277/10
See application file for complete search history.

(56) References Cited

U.S. PATENT DOCUMENTS

| | | | |
|---|---|---|---|
| 3,274,207 A | 9/1966 | Kollonitsch et al. |
| 3,809,754 A | 5/1974 | Bertrand |
| 3,882,110 A | 5/1975 | Clemence et al. |
| 4,270,537 A | 6/1981 | Romaine |
| 4,367,233 A | 1/1983 | Clark et al. |
| 4,406,905 A | 9/1983 | Zahner et al. |
| 4,457,935 A | 7/1984 | Iwao et al. |
| 4,457,936 A | 7/1984 | Draeger et al. |
| 4,558,059 A | 12/1985 | Kawasaki et al. |
| 4,596,556 A | 6/1986 | Morrow et al. |
| 4,736,060 A | 4/1988 | Tomuro et al. |
| 4,775,675 A | 10/1988 | Gyorgydeak et al. |
| 4,790,824 A | 12/1988 | Morrow et al. |
| 4,829,072 A | 5/1989 | Hamprecht et al. |
| 4,886,499 A | 12/1989 | Cirelli et al. |
| 4,902,700 A | 2/1990 | Hayasi et al. |
| 4,914,208 A | 4/1990 | Jakob et al. |
| 4,940,460 A | 7/1990 | Casey, I et al. |
| 4,941,880 A | 7/1990 | Burns |
| 5,015,235 A | 5/1991 | Crossman |
| 5,064,413 A | 11/1991 | McKinnon et al. |
| 5,084,083 A | 1/1992 | Lewis et al. |
| 5,106,992 A | 4/1992 | Magnin et al. |
| 5,141,496 A | 8/1992 | Dalto et al. |
| 5,169,858 A | 12/1992 | Rubin |
| 5,182,402 A | 1/1993 | Lewis et al. |
| 5,190,521 A | 3/1993 | Hubbard et al. |
| 5,192,781 A | 3/1993 | Bru-Magniez et al. |
| 5,312,335 A | 5/1994 | McKinnon et al. |
| 5,328,483 A | 7/1994 | Jacoby |
| 5,334,144 A | 8/1994 | Alchas et al. |
| 5,339,163 A | 8/1994 | Homma et al. |
| 5,383,851 A | 1/1995 | McKinnon, Jr. et al. |
| 5,385,922 A | 1/1995 | Bron et al. |
| 5,393,777 A | 2/1995 | Crosa |

(Continued)

FOREIGN PATENT DOCUMENTS

| | | |
|---|---|---|
| CA | 2728636 A1 | 1/2010 |
| CN | 101189216 A | 5/2008 |

(Continued)

OTHER PUBLICATIONS

Extended European Search Report, dated Jan. 19, 2010, in connection with Application No. EP 07874513.0.

(Continued)

*Primary Examiner* — Kamal A Saeed

(74) *Attorney, Agent, or Firm* — Robin L. Teskin; Baker, Donelson, Bearman, Caldwell & Berkowitz PC

(57) ABSTRACT

Macular degeneration, closed head injury, stroke, irritable bowel disease, and reperfusion injury are all associated with biological injury due to reactive oxygen species, probably due to focal iron overload in many instances. The present invention provides methods and pharmaceutical compositions for treating these diseases and conditions using desferrithiocin analogs of Formula (I). In certain embodiments, the analogs include a poly ether moiety at the 4'-position of the phenyl ring of the compound.

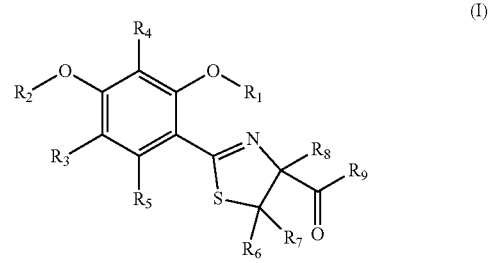

6 Claims, 4 Drawing Sheets

(56) References Cited

U.S. PATENT DOCUMENTS

| | | |
|---|---|---|
| 5,417,662 A | 5/1995 | Hjertman et al. |
| 5,442,073 A | 8/1995 | Eicken et al. |
| 5,466,220 A | 11/1995 | Brenneman |
| 5,480,381 A | 1/1996 | Weston |
| 5,503,627 A | 4/1996 | McKinnon et al. |
| 5,520,639 A | 5/1996 | Peterson et al. |
| 5,527,288 A | 6/1996 | Gross et al. |
| 5,569,189 A | 10/1996 | Parsons |
| 5,599,302 A | 2/1997 | Lilley et al. |
| 5,614,520 A | 3/1997 | Kondo et al. |
| 5,649,912 A | 7/1997 | Peterson |
| 5,704,911 A | 1/1998 | Parsons |
| 5,840,739 A | 11/1998 | Bergeron, Jr. |
| 5,893,397 A | 4/1999 | Peterson et al. |
| 5,993,412 A | 11/1999 | Deily et al. |
| 6,080,764 A | 6/2000 | Chihiro et al. |
| 6,083,966 A | 7/2000 | Bergeron, Jr. |
| 6,147,070 A | 11/2000 | Facchini |
| 6,159,983 A | 12/2000 | Bergeron, Jr. |
| 6,251,927 B1 | 6/2001 | Lai et al. |
| 6,437,143 B2 | 8/2002 | Moinet et al. |
| 6,521,652 B1 | 2/2003 | Bergeron |
| 6,525,080 B1 | 2/2003 | Bergeron |
| 6,559,315 B1 | 5/2003 | Bergeron |
| 6,864,270 B2 | 3/2005 | Bergeron, Jr. |
| RE39,132 E | 6/2006 | Bergeron, Jr. |
| 7,126,004 B2 | 10/2006 | Bergeron |
| 7,141,589 B2 | 11/2006 | Park et al. |
| 7,144,904 B2 | 12/2006 | Bergeron, Jr. |
| 7,531,563 B2 | 5/2009 | Bergeron |
| 7,879,886 B2 | 2/2011 | Bergeron, Jr. |
| 8,008,502 B2 | 8/2011 | Bergeron |
| 8,063,227 B2 | 11/2011 | Tapper et al. |
| 8,278,458 B2 | 10/2012 | Bergeron, Jr. |
| 8,324,397 B2 | 12/2012 | Bergeron, Jr. |
| 8,604,216 B2 | 12/2013 | Bergeron, Jr. |
| 8,722,899 B2 | 5/2014 | Bergeron, Jr. |
| 9,096,553 B2 | 8/2015 | Bergeron, Jr. |
| 9,174,948 B2 | 11/2015 | Bergeron, Jr. |
| 9,567,309 B2 | 2/2017 | Bergeron, Jr. |
| 9,730,917 B2 | 8/2017 | Bergeron, Jr. |
| 9,994,535 B2 | 6/2018 | Bergeron, Jr. |
| 10,010,535 B2 | 7/2018 | Bergeron, Jr. |
| 10,570,104 B2 | 2/2020 | Bergeron, Jr. |
| 2002/0049316 A1 | 4/2002 | Halbert et al. |
| 2003/0083349 A1 | 5/2003 | Bergeron, Jr. |
| 2003/0236417 A1 | 12/2003 | Bergeron |
| 2004/0044220 A1 | 3/2004 | Bergeron |
| 2004/0132789 A1 | 7/2004 | Bergeron |
| 2005/0033057 A1 | 2/2005 | Bergeron |
| 2005/0234113 A1 | 10/2005 | Bergeron |
| 2006/0211746 A1 | 9/2006 | Bergeron |
| 2006/0211773 A1 | 9/2006 | Bergeron, Jr. |
| 2007/0238767 A1 | 10/2007 | Bergeron |
| 2008/0096974 A2 | 4/2008 | Bergeron, Jr. |
| 2008/0194518 A1 | 8/2008 | Mookerjee et al. |
| 2008/0214630 A1 | 9/2008 | Bergeron |
| 2008/0255081 A1 | 10/2008 | Bergeron, Jr. |
| 2010/0093812 A1 | 4/2010 | Bergeron, Jr. |
| 2010/0094016 A1 | 4/2010 | Bergeron |
| 2010/0137346 A1 | 6/2010 | Bergeron, Jr. |
| 2010/0137383 A1 | 6/2010 | Tapper et al. |
| 2011/0053993 A1 | 3/2011 | McCall, Jr. et al. |
| 2011/0275636 A1 | 11/2011 | Malecha |
| 2012/0184586 A1 | 7/2012 | Bergeron, Jr. |
| 2013/0030028 A1 | 1/2013 | Bergeron, Jr. |
| 2013/0210870 A1 | 8/2013 | Bergeron, Jr. |
| 2014/0235680 A1 | 8/2014 | Bergeron, Jr. |
| 2014/0323534 A1 | 10/2014 | Bergeron, Jr. |
| 2014/0343110 A1 | 11/2014 | Bergeron, Jr. |
| 2015/0336911 A1 | 11/2015 | Bergeron, Jr. |
| 2016/0022645 A1 | 1/2016 | Bergeron, Jr. |
| 2016/0289223 A1 | 10/2016 | Bergeron, Jr. |
| 2017/0209420 A1 | 7/2017 | Bergeron, Jr. |
| 2017/0217912 A1 | 8/2017 | Bergeron, Jr. |
| 2018/0140581 A1 | 5/2018 | Bergeron, Jr. |
| 2018/0290990 A1 | 10/2018 | Bergeron, Jr. |

FOREIGN PATENT DOCUMENTS

| | | |
|---|---|---|
| CN | 101687825 A | 3/2010 |
| CN | 102149700 A | 8/2011 |
| CN | 102574824 A | 7/2012 |
| CN | 102648189 A | 8/2012 |
| CN | 104114170 A | 10/2014 |
| DE | 2245560 A1 | 3/1974 |
| DE | 3002989 A1 | 7/1981 |
| EP | 0214101 A2 | 3/1987 |
| EP | 0214933 A2 | 3/1987 |
| EP | 0325559 A2 | 7/1989 |
| EP | 0513379 A1 | 11/1992 |
| EP | 2062581 A1 | 5/2009 |
| FR | 2247243 A2 | 5/1975 |
| GB | 1292170 A | 10/1972 |
| GB | 1382887 A | 2/1975 |
| JP | 57-058682 A | 4/1982 |
| JP | 2000-505086 A | 4/2000 |
| JP | 2002-523500 A | 7/2002 |
| JP | 2008-536833 A | 9/2008 |
| JP | 2010-521471 A | 6/2010 |
| JP | 2011-528037 A | 11/2011 |
| JP | 2013-500342 A | 1/2013 |
| JP | 2013-503160 A | 1/2013 |
| JP | 2013-525495 A | 6/2013 |
| JP | 5909473 B2 | 4/2016 |
| WO | WO 1994/011367 A1 | 5/1994 |
| WO | WO 1997/036885 A1 | 10/1997 |
| WO | WO 1999/053039 A1 | 10/1999 |
| WO | WO 2000/012493 A1 | 3/2000 |
| WO | WO 2000/016763 A2 | 3/2000 |
| WO | WO 2001/027119 A2 | 4/2001 |
| WO | WO 2003/078467 A1 | 9/2003 |
| WO | WO 2004/017959 A2 | 3/2004 |
| WO | WO 2005/023310 A2 | 3/2005 |
| WO | WO 2005/034949 A1 | 4/2005 |
| WO | WO 2006/055412 A1 | 5/2006 |
| WO | WO 2006/107626 A1 | 10/2006 |
| WO | WO 2008/115433 A1 | 9/2008 |
| WO | WO 2008/130395 A2 | 10/2008 |
| WO | WO 2009/053628 A2 | 4/2009 |
| WO | WO 2009/140215 A2 | 11/2009 |
| WO | WO 2009/155088 A1 | 12/2009 |
| WO | WO 2010/009120 A2 | 1/2010 |
| WO | WO 2011/017054 A2 | 2/2011 |
| WO | WO 2011/028255 A2 | 3/2011 |
| WO | WO 2012/027794 A2 | 3/2012 |
| WO | WO 2013/086312 A1 | 6/2013 |
| WO | WO 2013/090750 A1 | 6/2013 |
| WO | WO 2013/090766 A1 | 6/2013 |
| WO | WO 2014/027355 A2 | 2/2014 |
| WO | WO 2014/134701 A1 | 9/2014 |

OTHER PUBLICATIONS

International Search Report and Written Opinion, dated Jan. 8, 2009, in connection with Application No. PCT/US2007/025377.
International Preliminary Report on Patentability, dated Jun. 23, 2009, in connection with Application No. PCT/US2007/025377.
Extended European Search Report, dated Dec. 27, 2010, in connection with Application No. EP 08742093.1.
International Search Report and Written Opinion, dated Jun. 19, 2008, in connection with Application No. PCT/US2008/003433.
International Preliminary Report on Patentability, dated Sep. 24, 2009, in connection with Application No. PCT/US2008/003433.
Supplementary European Search Report, dated Dec. 5, 2001, in connection with Application No. EP 99945267.5.
International Search Report, dated Jan. 19, 2000, in connection with Application No. PCT/US1999/019691.
Written Opinion, dated Aug. 21, 2000, in connection with Application No. PCT/US1999/019691.

(56) References Cited

OTHER PUBLICATIONS

International Preliminary Examination Report, dated Feb. 2, 2001, in connection with Application No. PCT/US1999/019691.
Extended European Search Report, dated Mar. 25, 2013, in connection with Application No. EP 10814064.1.
International Search Report and Written Opinion, dated May 23, 2011, in connection with Application No. PCT/US2010/002336.
International Preliminary Report on Patentability, dated Mar. 8, 2012, in connection with Application No. PCT/US2010/002336.
International Search Report and Written Opinion, dated Mar. 5, 2004, in connection with Application No. PCT/US2003/028304.
Extended European Search Report, dated Mar. 29, 2017, in connection with Application No. EP 16196408.5.
International Search Report and Written Opinion, dated Aug. 9, 2006, in connection with Application No. PCT/US2006/010945.
International Preliminary Report on Patentability, dated Oct. 18, 2007, in connection with Application No. PCT/US2006/010945.
European Search Report, dated Mar. 20, 2015, in connection with Application No. EP 12857135.3.
Extended European Search Report, dated Jul. 9, 2015, in connection with Application No. EP 12857135.3.
Extended European Search Report, dated Feb. 6, 2020, in connection with Application No. EP 19182850.8.
International Search Report and Written Opinion, dated Apr. 19, 2013, in connection with Application No. PCT/US2012/069795.
International Preliminary Report on Patentability, dated Jun. 26, 2014, in connection with Application No. PCT/US2012/069795.
International Search Report and Written Opinion, dated Apr. 12, 2013, in connection with Application No. PCT/US2012/069826.
International Preliminary Report on Patentability, dated Jun. 26, 2014, in connection with Application No. PCT/US2012/069826.
Invitation to Pay Additional Fees, dated Jan. 27, 2015, in connection with Application No. PCT/US2014/066961.
International Search Report and Written Opinion, dated Apr. 14, 2015, in connection with Application No. PCT/US2014/066961.
Extended European Search Report, dated Mar. 29, 2017, in connection with Application No. EP 14864521.1.
Invitation to Pay Additional Fees, dated Jan. 27, 2015, in connection with Application No. PCT/US2014/066965.
International Search Report and Written Opinion, dated Apr. 14, 2015, in connection with Application No. PCT/US2014/066965.
International Preliminary Report on Patentability dated Oct. 5, 2017, in connection with Application No. PCT/US2016/024239.
International Search Report and Written Opinion, dated Jun. 17, 2016, in connection with Application No. PCT/US2016/024239.
International Search Report and Written Opinion, dated Sep. 23, 2016, in connection with Application No. PCT/US2016/029587.
International Preliminary Report, dated Nov. 9, 2017, in connection with Application No. PCT/US2016/029587.
Extended European Search Report, dated Oct. 8, 2018, in connection with Application No. EP 16787077.3.
[No Author Listed] Chemcats, Accession No. 2003:2524667; TimTec Overseas Stock; May 19, 2003.
[No Author Listed] Desferal. Product Information. Novartis Pharmaceuticals Corporation. East Hanover, NJ. 2011. Available at www.pharma.us.novartis.com/product/pi/pdf/desferal.pdf. Last accessed Jan. 25, 2013.
[No Author Listed] Highlights of Prescribing Information: EXJADE. Novartis Pharma Stein AG. 2010. Available at http://www.pharma.us.novartis.com/product/pi/pdf/exjade.pdf. Last accessed Sep. 9, 2010. 14 pages.
[No Author Listed] "Ion exchanger." Ullmanns Encyclopedia of Industrial Chemistry. 5th Ed. vol. 14A:446-56.
[No Author Listed], Closed head injury. Wikipedia. http://en.wikipedia.org/wiki/Close_head_injury [last accessed Nov. 28, 2011]. 7 pages.
[No Author Listed], Irritable bowel syndrome. Wikipedia. http://en.wikipedia.org/wiki/Irritable_bowel_syndrome [last accessed Nov. 28, 2011]. 24 pages.

[No Author Listed], Macular degeneration. Wikipedia. http://en.wikipedia.org/wiki/Macular_degeneration [last accessed Nov. 28, 2011]. 14 pages.
[No Author Listed], Reperfusion injury. Wikipedia. http://en.wikipedia.org/wiki/Reperfusion_injury [last accessed Nov. 28, 2011]. 7 pages.
[No Author Listed], Stroke. Wikipedia. http://en.wikipedia.org/wiki/Stroke [last accessed Nov. 28, 2011]. 29 pages.
Abergel et al., Anthrax pathogen evades the mammalian immune system through stealth siderophore production. Proc Natl Acad Sci U S A. Dec. 5, 2006;103(49):18499-503. Epub Nov. 28, 2006.
Allgayer, Clinical relevance of oxygen radicals in inflammatory bowel disease—facts and fashion. Klin Wochenschr. Dec. 15, 1991;69(21-23):1001-3.
Al-Refaie et al., Zinc concentration in patients with iron overload receiving oral iron chelator 1,2-dimethyl-3-hydroxypyrid-4-one or desferrioxamine. J Clin Pathol. 1994;47:657-60.
Anderegg et al., Metal Complex Formation of a New Siderophore Desferrithiocin and of Three Related Ligands. J Chem Soc Chem Commun. 1990:1194-6.
Andrews et al., Iron homeostasis. Annu Rev Physiol. 2007;69:69-85.
Angelucci et al., Hepatic iron concentration and total body iron stores in thalassemia major. N Engl J Med. Aug. 3, 2000;343(5):327-31.
Babbs et al., Oxygen radicals in ulcerative colitis. Free Radic Biol Med. 1992;13(2):169-81.
Baker et al., Desferrithiocin is an effective iron chelator in vivo and in vitro but ferrithiocin is toxic. Br J Haematol. Jul. 1992;81(3):424-31.
Barman-Balfour et al., Deferiprone: a review of its clinical potential in iron overload in beta-thalassaemia major and other transfusion-dependent diseases. Drugs. Sep. 1999;58(3):553-78.
Bartakke et al., Effect of Deferiprone on Urinary Zinc Excretion in Multiply Transfused Children with Thalassemia Major. Ind Ped. Feb. 17, 2005;42:150-4.
Bauer et al., Iron Complexes in Organic Chemistry. Ed:Plietker. 2008;1-27.
Bedford et al., Iron chelation in the treatment of cancer: a new role for deferasirox? J Clin Pharmacol. Sep. 2013;53(9):885-91. doi: 10.1002/jeph.113. Epub Jun. 6, 2013.
Berge et al., Pharmaceutical salts. J Pharm Sci. Jan. 1977;66(1):1-19.
Bergeron et al., (S)-4,5-dihydro-2-(2-hydroxy-4-hydroxyphenyl)-4-methyl-4-thiazolecarboxylic acid polyethers: a solution to nephrotoxicity. J Med Chem. May 4, 2006;49(9):2772-83.
Bergeron et al., A comparative evaluation of iron clearance models. Ann N Y Acad Sci. 1990;612:378-93.
Bergeron et al., A comparative study of the iron-clearing properties of desferrithiocin analogues with desferrioxamine B in a Cebus monkey model. Blood. Apr. 15, 1993;81(8):2166-73.
Bergeron et al., A comparison of the iron-clearing properties of 1,2-dimethyl-3-hydroxypyrid-4-one, 1,2-diethyl-3-hydroxypyrid-4-one, and deferoxamine. Blood. Apr. 1, 1992;79(7):1882-90.
Bergeron et al., An efficient total synthesis of Desferrioxamine B. J Organic Chemistry. 1988;53(14):3131-3134.
Bergeron et al., An investigation of desferrithiocin metabolism. J Med Chem. Sep. 2, 1994;37(18):2889-95.
Bergeron et al., Comparison of iron chelator efficacy in iron-overloaded beagle dogs and monkeys (*Cebus apella*). Comp Med. Dec. 2004;54(6):664-72.
Bergeron et al., Desazadesmethyldesferrithiocin Analogues as Orally Effective Iron Chelators. J Med Chem. 1999;42:95-108.
Bergeron et al., Desferrithiocin analogue based hexacoordinate iron(III) chelators. J Med Chem. Jan. 2, 2003;46(1):16-24.
Bergeron et al., Desferrithiocin analogue iron chelators: iron clearing efficiency, tissue distribution, and renal toxicity. Biometals. Apr. 2011;24(2):239-58. Epub Nov. 20, 2010.
Bergeron et al., Desferrithiocin analogue uranium decorporation agents. Int J Radiat Biol. Apr. 2009;85(4):348-61.
Bergeron et al., Desferrithiocin analogues and nephrotoxicity. J Med Chem. Oct. 9, 2008;51(19):5993-6004. Epub Sep. 13, 2008.

(56) References Cited

OTHER PUBLICATIONS

Bergeron et al., Desferrithiocin: a search for clinically effective iron chelators. J Med Chem. Nov. 26, 2014;57(22):9259-91. doi:10.1021/jm500828f. Epub Sep. 10, 2014.
Bergeron et al., Design, synthesis, and testing of non-nephrotoxic desazadesferrithiocin polyether analogues. J Med Chem. Jul. 10, 2008;51(13):3913-23. Epub Jun. 6, 2008.
Bergeron et al., Design, Synthesis, and Testing of Polyamine Vectored Iron Chelators. Synthesis (Stuttg). 2010;2010(21):3631-3636.
Bergeron et al., Effects of C-4 stereochemistry and C-4' hydroxylation on the iron clearing efficiency and toxicity of desferrithiocin analogues. J Med Chem. Jul. 1, 1999;42(13):2432-40.
Bergeron et al., Evaluation of desferrithiocin and its synthetic analogues as orally effective iron chelators. J Med Chem. Jul. 1991;34(7):2072-8.
Bergeron et al., Evaluation of the desferrithiocin pharmacophore as a vector for hydroxamates. J Med Chem. Jul. 29, 1999;42(15):2881-6.
Bergeron et al., HBED: A Potential Alternative to Deferoxamine for Iron-Chelating Therapy. Blood. 1998;91:1446-52.
Bergeron et al., Impact of the 3,6,9-Trioxadecyloxy Group on Desazadesferrithiocin Analogue Iron Clearance and Organ Distribution. J Med Chem. Jul. 12, 2007;50(14):3302-13. Epub Jun. 12, 2007.
Bergeron et al., Impact of the Lipophilicity of Desferrithiocin Analogues on Iron Clearance. Medicinal Inorg Chem. 2005:366-83.
Bergeron et al., Influence of iron on in vivo proliferation and lethality of L1210 cells. J Nutr. Mar. 1985;115(3):369-74.
Bergeron et al., Iron chelation promoted by desazadesferrithiocin analogs: An enantioselective barrier. Chirality. Aug. 2003;15(7):593-9.
Bergeron et al., Iron Chelators and Therapeutic Uses. In: Burger's Medicinal Chemistry, 6th ed. 2003:479-561.
Bergeron et al., Metabolism and pharmacokinetics of N1,N11-diethylnorspermine in a Cebus apella primate model. Cancer Res. Aug. 15, 2000;60(16):4433-9.
Bergeron et al., Metabolism and pharmacokinetics of N1,N14-diethylhomospermine. Drug Metab Dispos. Mar. 1996;24(3):334-43.
Bergeron et al., Methoxylation of desazadesferrithiocin analogues: enhanced iron clearing efficiency. J Med Chem. Apr. 10, 2003;46(8):1470-7.
Bergeron et al., Partition-variant desferrithiocin analogues: organ targeting and increased iron clearance. J Med Chem. Feb. 10, 2005;48(3):821-31.
Bergeron et al., Pharmacokinetics of orally administered desferrithiocin analogs in cebus apella primates. Drug Metab Dispos. Dec. 1999;27(12):1496-8.
Bergeron et al., Polyamine-vectored iron chelators: the role of charge. J Med Chem. Jun. 16, 2005;48(12):4120-37.
Bergeron et al., Prevention of acetic acid-induced colitis by desferrithiocin analogs in a rat model. Dig Dis Sci. Feb. 2003;48(2):399-407.
Bergeron et al., Structure-activity relationships among desazadesferrithiocin analogues. In: Iron Chelation Therapy. Hershko, ed. 2002:167-84.
Bergeron et al., Substituent effects on desferrithiocin and desferrithiocin analogue iron-clearing and toxicity profiles. J Med Chem. Aug. 23, 2012;55(16):7090-103. doi: 10.1021/jm300509y. Epub Aug. 13, 2012.
Bergeron et al., Synthesis and biological evaluation of hydroxamate-based iron chelators. J Med Chem. Nov. 1991;34(11):3182-7.
Bergeron et al., Synthesis and biological evaluation of naphthyldesferrithiocin iron chelators. J Med Chem. Apr. 12, 1996;39(8):1575-81.
Bergeron et al., Synthesis of heterobactins A and B and Nocardia heterobactin. Tetrahedron. 2011:67(18):3163-69.
Bergeron et al., The desferrithiocin pharmacophore. J Med Chem. May 13, 1994;37(10):1411-7.
Bergeron et al., The design, synthesis, and evaluation of organ-specific iron chelators. J Med Chem. Nov. 30, 2006;49(24):7032-43.
Bergeron et al., The impact of polyether chain length on the iron clearing efficiency and physiochemical properties of desferrithiocin analogues. J Med Chem. Apr. 8, 2010;53(7):2843-53.
Bergeron et al., The origin of the differences in (R)- and (S)-desmethyldesferrithiocin. Iron-clearing properties. Ann N Y Acad Sci. Jun. 30, 1998;850:202-16.
Bergeron et al., Vibriobactin antibodies: a vaccine strategy. J Med Chem. Jun. 25, 2009;52(12):3801-13.
Bergeron, Desferrithiocin Polyether Analogue Uranium Decorporation Agents. Quad Chart and White Paper. Research Area #4 Radiological/Nuclear Threat Medical Countermeasures. BARDA CBRN BAA-11-100-SOL-00009. Oct. 27, 2011. 17 pages.
Bergeron, Iron: A Controlling Nutrient in Proliferative Processes. Trends in Biochem Sci. 1986;11:133-36.
Bickel et al., [Metabolic Properties of Actinomycetes.] Ferrioxamine B. Helv Chim Acta. 1960;43:2129-38. German.
Bierer et al., The effect of desferrithiocin, an oral iron chelator, on T-cell function. Blood. Nov. 15, 1990;76(10):2052-9.
Boddaert et al., Selective iron chelation in Friedreich ataxia: biologic and clinical implications. Blood. Jul. 1, 2007;110(1):401-8. Epub Mar. 22, 2007.
Bolli et al., Iron-mediated radical reactions upon reperfusion contribute to myocardial "stunning". Am J Physiol. Dec. 1990;259(6 Pt 2):H1901-11.
Bonkovsky et al., Iron-induced liver injury. Clin Liver Dis. May 2000;4(2):409-29, vi-vii.
Brissot et al., Non-transferrin bound iron: a key role in iron overload and iron toxicity. Biochim Biophys Acta. Mar. 2012;1820(3):403-10. doi: 10.1016/j.bbagen.2011.07.014. Epub Aug. 9, 2011.
Brittenham et al., Efficacy of deferoxamine in preventing complications of iron overload in patients with thalassemia major. N Engl J Med. Sep. 1, 1994;331(9):567-73.
Brittenham, Disorders of Iron Metabolism: Iron Deficiency and Overload. In: Hematology: Basic Principles and Practice. 3d Ed. Hoffman et al., eds., Churchill Livingston. New York. 2000:397-428.
Brittenham, Iron chelators and iron toxicity. Alcohol. Jun. 2003;30(2):151-8.
Brittenham, Pyridoxal isonicotinoyl hydrazone. Effective iron chelation after oral administration. Ann N Y Acad Sci. 1990;612:315-26.
Brittenham, Pyridoxal isonicotinoyl hydrazone: an effective iron-chelator after oral administration. Semin Hematol. Apr. 1990;27(2):112-6.
Brunner et al., Carboplatin-containing Porphyrin-platinum Complexes as Cytotoxic and Phototoxic Antitumor Agents. Inorg Chim Acta. 2004;357:4423-51.
Bucolo et al., Ocular drug delivery: a clue from nanotechnology. Frontiers in Pharmacology. Oct. 25, 2012;3(188):1-3.
Budimir, Metal ions, Alzheimer's disease and chelation therapy. Acta Pharm. Mar. 2011;61(1):1-14. doi: 10.2478/v10007-011-0006-6.
Byers et al., Microbial iron transport: iron acquisition by pathogenic microorganisms. Met Ions Biol Syst. 1998;35:37-66.
Cappellini et al., Oral iron chelators. Annu Rev Med. 2009;60:25-38. doi: 10.1146/annurev.med.60.041807.123243.
Cappellini, Iron-chelating therapy with the new oral agent ICL670 (Exjade). Best Pract Res Clin Haematol. Jun. 2005;18(2):289-98.
Cario, Insulin sensitivity and beta-cell secretion in thalassaemia major with secondary haemochromatosis: assessment by oral glucose tolerance test. Eur J Pediatr. Mar. 2003;162(3):139-46. Epub Jan. 15, 2003.
Cavaliere et al., The biofilm matrix destabilizers, EDTA and DNaseI, enhance the susceptibility of nontypeable Hemophilus influenzae biofilms to treatment with ampicillin and ciprofloxacin. Microbiologyopen. Aug. 2014;3(4):557-67. doi: 10.1002/mbo3.187. Epub Jul. 6, 2014.
Chua et al., Nontransferrin-bound iron uptake by hepatocytes is increased in the Hfe knockout mouse model of hereditary hemochromatosis. Blood. Sep. 1, 2004;104(5):1519-25. Epub May 20, 2004.

(56) References Cited

OTHER PUBLICATIONS

Conrad et al., Iron absorption and transport. Am J Med Sci. Oct. 1999;318(4):213-29.
Cragg et al., The iron chelator L1 potentiates oxidative DNA damage in iron-loaded liver cells. Blood. Jul. 15, 1998;92(2):632-8.
Cunningham et al., New developments in iron chelators. Curr Opin Hematol. Mar. 2005;12(2):129-34.
Dean et al., The Action of Nine Chelators on Iron-Dependent Radical Damage. Free Rad Res. 1994;20(2):83-101.
Dolai et al., Water-stable manganese(IV) complex of a N2O4-donor non-Schiff-base ligand: synthesis, structure, and multifrequency high-field electron paramagnetic resonance studies. Inorg Chem. Jun. 2, 2014;53(11):5423-8. doi: 10.1021/ic4030958. Epub May 13, 2014.
Dolakova et al., Synthesis of Analogues of Acyclic Nucleoside Diphosphates Containing a (Phosphonomethyl)phosphanyl Moiety and Studies of Their Phosphorylation. EurJOC. 2009;1082-1092.
Domingo et al., Comparative effects of the chelators sodium 4,5-dihydroxybenzene-1,3-disulfonate (Tiron) and diethylenetriaminepentaacetic acid (DTPA) on acute uranium nephrotoxicity in rats. Toxicology. Mar. 14, 1997;118(1):49-59.
Donovan et al., Preclinical and clinical development of deferitrin, a novel, orally available iron chelator. Ann N Y Acad Sci. 2005;1054:492-4.
Dunaief et al., Macular degeneration in a patient with aceruloplasminemia, a disease associated with retinal iron overload. Ophthalmology. Jun. 2005;112(6):1062-5.
Dunaief, Iron induced oxidative damage as a potential factor in age-related macular degeneration: the Cogan Lecture. Invest Ophthalmol Vis Sci. Nov. 2006;47(11):4660-4.
Durbin et al., Chelating agents for uranium(VI): 2. Efficacy and toxicity of tetradentate catecholate and hydroxypyridinonate ligands in mice. Health Phys. May 2000;78(5):511-21.
Durbin et al., In Vivo Chelation of Am(III), Pu(IV), Np(V), and U(VI) in Mice by TREN-(Me-3,2-HOPO). Radiat Prot Dosimetry. 1994;53:305-09.
Durbin, Lauriston S. Taylor Lecture: the quest for therapeutic actinide chelators. Health Phys. Nov. 2008;95(5):465-92.
Farkas et al., Structure-based differences between the metal ion selectivity of two siderophores desferrioxamine B (DFB) and desferricoprogen (DFC): Why DFC is much better Pb(II) sequestering agent than DFB? J Inorg Biochem. 2008;102;1654-9.
Fedorak et al., Misoprostol provides a colonic mucosal protective effect during acetic acid-induced colitis in rats. Gastroenterology. Mar. 1990;98(3):615-25.
Ferreira Pimentel et al., Synthesis, structural and spectroscopic studies of BNSalanH2 and BPSalanH2. Zeitschrift für Kristallographie—Crystalline Materials. 2010;225(6):240-4. doi: https://doi.org/10.1524/zkri.2010.1231.
Finch et al., Ferrokinetics in man. Medicine (Baltimore). Jan. 1970;49(1):17-53.
Finch et al., Iron metabolism. Clin Physiol Biochem. 1986;4(1):5-10.
Finch et al., Perspectives in iron metabolism. N Engl J Med. Jun. 24, 1982;306(25):1520-8.
Fritsch et al., Plasmodium falciparum: inhibition in vitro with lactoferrin, desferriferrithiocin, and desferricrocin. Exp Parasitol. Feb. 1987;63(1):1-9.
Fukuda, Chelating agents used for plutonium and uranium removal in radiation emergency medicine. Curr Med Chem. 2005;12(23):2765-70.
Galanello et al., A dose escalation study of the pharmacokinetics, safety & efficacy of deferitrin, an oral iron chelator in beta thalassaemia patients. ASH Annu Meet Abstr. 2007;110: Abstract 2669.
Galanello et al., Safety, tolerability, and pharmacokinetics of ICL670, a new orally active iron-chelating agent in patients with transfusion-dependent iron overload due to beta-thalassemia. J Clin Pharmacol. Jun. 2003;43(6):565-72.
Galey et al., N,N'-bis-(3,4,5-trimethoxybenzyl) ethylenediamine N,N'-diacetic acid as a new iron chelator with potential medicinal applications against oxidative stress. Biochem Pharmacol. Jan. 26, 1996;51(2):103-15.
Ganeshpure et al., N,N?-Bis(2-hydroxybenzyl)ethylenediamine-N,N?-dipropionic acid. A new chelating ligand for iron(III). Transition Metal Chemisry. Jun. 1992;17:212-215.
Gaudana et al., Ocular drug delivery. AAPS J. Sep. 2010;12(3):348-60. doi: 10.1208/s12248-010-9183-3. Epub May 1, 2010.
Gershon et al., Antifungal activity of 5-, 7-, and 5,7-substituted 2-methyl-8-quinolinols. Antimicrob Agents Chemother. May 1972;1(5):373-5.
Giardina et al., Chelation therapy in beta-thalassemia: an optimistic update. Semin Hematol. Oct. 2001;38(4):360-6.
Gkouvatsos et al., Regulation of iron transport and the role of transferrin. Biochim Biophys Acta. Mar. 2012;1820(3):188-202. doi: 10.1016/j.bbagen.2011.10.013. Epub Nov. 4, 2011.
Golchoubian et al., Synthesis and characterization of mono- and bimetallic complexes of Zn(II) and Cu(II); new multifunctional unsymmetrical acyclic and macrocyclic phenol-based ligand. Current Chemistry Letters. 2013;2(4):207-14.
Gorden et al., Rational design of sequestering agents for plutonium and other actinides.Chem Rev. Nov. 2003;103(11):4207-82.
Grady et al., HBED: a potential oral iron chelator. Ann N Y Acad Sci. 1990;612:361-8.
Grady et al., Rhodotorulic acid—investigation of its potential as an iron-chelating drug. J Pharmacol Exp Ther. Jun. 1979;209(3):342-8.
Graf et al., Iron-catalyzed hydroxyl radical formation. Stringent requirement for free iron coordination site. J Biol Chem. Mar. 25, 1984;259(6):3620-4.
Grisham et al., Neutrophil-mediated mucosal injury. Role of reactive oxygen metabolites. Dig Dis Sci. Mar. 1988;33(3 Suppl):6S-15S.
Guilmette et al., Competitive binding of Pu and Am with bone mineral and novel chelating agents. Radiat Prot Dosimetry. 2003;105(1-4):527-34.
Guterman et al., Feasibility of enterochelin as an iron-chelating drug: studies with human serum and a mouse model system. Gen Pharmacol. 1978;9(2):123-7.
Hadziahmetovic et al., The oral iron chelator deferiprone protects against iron overload-induced retinal degeneration. Invest Ophthalmol Vis Sci. Feb. 16, 2011;52(2):959-68. doi: 10.1167/iovs.10-6207.
Hahn et al., Coordination Chemistry of Microbial Iron Transport. 42. Structural and Spectroscopic Characterization of Diastereomeric Cr(III) and Co(III) Complexes of Desferriferrithiocin. J Am Chem Soc. 1990;112:1854-60.
Hall et al., Antioxidant therapies for traumatic brain injury. Neurotherapeutics. Jan. 2010;7(1):51-61. doi: 10.1016/j.nurt.2009.10.021.
Hallberg, Bioavailability of dietary iron in man. Ann Rev Nutr. 1981;1:123-47.
Halliwell, Free radicals and antioxidants: a personal view. Nutr Rev. Aug. 1994;52(8 Pt 1):253-65.
Halliwell, Iron, Oxidative Damage and Chelating Agents. In: The Development of Iron Chelators for Clinical Use, Bergeron, ed. 1994:33-56.
He et al., A fluorescent chemosensor for calcium with excellent storage stability in water. Anal Chim Acta. Mar. 24, 2008;611(2):197-204. doi:10.1016/j.aca.2008.01.059. Epub Feb. 2, 2008.
He et al., Iron homeostasis and toxicity in retinal degeneration. Prog. Retin. Eye Res. Nov. 2007;26(6):649-73. Epub Aug. 11, 2007.
Henry, Chemotherapeutic nitroheterocycles. Derivatives of 5-nitrothiazole-2-carboxaldehyde and 5-nitrothiazole-2-carboxylic acid. J Med Chem. Mar. 1969;12(2):303-6.
Hoffbrand et al., Long-term trial of deferiprone in 51 transfusion-dependent iron overloaded patients. Blood. Jan. 1, 1998;91(1):295-300.
Hoffbrand, Transfusion Siderosis and Chelation Therapy. Iron in Biochemistry and Medicine. vol. II. London. 1980: 449-527.
Horackova et al., The antioxidant effects of a novel iron chelator salicylaldehyde isonicotinoyl hydrazone in the prevention of H(2)O(2) injury in adult cardiomyocytes. Cardiovasc Res. Aug. 18, 2000;47(3):529-36.

(56) References Cited

OTHER PUBLICATIONS

Hua et al., Long-term effects of experimental intracerebral hemorrhage: the role of iron. J Neurosurg. Feb. 2006;104(2):305-12.

Iranmanesh et al., Chelation of chromium(VI) by combining deferasirox and deferiprone in rats. Biometals. 2013;26:465-71.

Jalal et al., Structure of Anguibactin, a Unique Plasmid-Related Bacterial Siderophore from the Fish Pathogen Vibrio Anguillarum. J Am Chem Soc. 1989;111(1):292-96.

Jarvis et al., Some correlations involving the stability of complexes of transuranium metal ions and ligands with negatively charged oxygen donors. Inorg Chim Acta. 1991;182:229-32.

Jomova et al., Advances in metal-induced oxidative stress and human disease. Toxicology. May 10, 2011;283(2-3):65-87. doi: 10.1016/j.tox.2011.03.001. Epub Mar. 23, 2011.

Joo Suk, Paradoxical hypomagnesemia caused by excessive ingestion of magnesium hydroxide. Am J Emerg Med. Sep. 2008;26(7):837.e1-2. doi:10.1016/j.ajem.2008.01.030.

Kalinowski et al., The evolution of iron chelators for the treatment of iron overload disease and cancer. Pharmacol Rev. Dec. 2005;57(4):547-83.

Kem et al., Hydroxy metabolites of the Alzheimer's drug candidate 3-[(2,4-dimethoxy)benzylidene]-anabaseine dihydrochloride (GTS-21): their molecular properties, interactions with brain nicotinic receptors, and brain penetration. Mol Pharmacol. Jan. 2004;65(1):56-67.

Kersten et al., Long-term treatment of transfusional iron overload with the oral iron chelator deferiprone (L1): a Dutch multicenter trial. Ann Hematol. Nov. 1996;73(5):247-52.

Kicic et al., The desferrithiocin (DFT) class of iron chelators: potential as antineoplastic agents. Anticancer Drug Des. Aug.-Oct. 2001;16(4-5):195-207.

Kishore et al., Synthesis of α-Poly-[Nε-2-aryl-Δ2-thiazoline-4-carbonyl-L-lysine] with Antival Activity. Ind J Chem. 1977;15B:255-57.

Kitazawa et al., Reduction of ultraviolet light-induced oxidative stress by amino acid-based iron chelators. Biochim Biophys Acta. Dec. 27, 1999;1473(2-3):400-8.

Koide et al., Development of novel EDG3 antagonists using a 3D database search and their structure-activity relationships. J Med Chem. Oct. 10, 2002;45(21):4629-38.

Kontoghiorghes et al., 1,2-Dimethyl-3-hydroxypyrid-4-one, an orally active chelator for treatment of iron overload. Lancet. Jun. 6, 1987;1(8545):1294-5.

Kontoghiorghes, New Concepts of Iron and Aluminium Chelation Therapy With Oral L1 (Deferiprone) and Other Chelators. Analyst. Mar. 1995;120:845-51.

Koppenol, Kinetics and Mechanisms of the Fenton Reaction: Implications in Iron Toxicity. In: Iron Chelators: New Development Strategies, Bergeron, ed., 2000:3-10.

Langer et al., Solid complexes with tetravalent metal ions and ethylenediamime tetra-acetic acid (EDTA). J Inorg Nucl Chem. 1964;26:59-72.

Levien et al., Pentetate Calcium Trisodium (Ca-DTPA) and Pentetate Zinc Trisodium (Zn-DTPA). Formulary Drug Reviews. 2005;40:65-71.

Li et al., Binding and uptake of H-ferritin are mediated by human transferrin receptor-1. Proc Natl Acad Sci U S A. Feb. 23, 2010;107(8):3505-10. doi: 10.1073/pnas.0913192107. Epub Feb. 4, 2010.

Lieu et al., The roles of iron in health and disease. Mol Aspects Med. Feb.-Apr. 2001;22(1-2):1-87.

Liu et al., Nanoparticle and iron chelators as a potential novel Alzheimer therapy. Methods Mol Biol. 2010;610:123-44. doi: 10.1007/978-1-60327-029-8_8.

Long et al., Deferoxamine improves spatial memory performance following experimental brain injury in rats. Brain Res. Apr. 22, 1996;717(1-2):109-17.

Lovejoy et al., Iron chelators as anti-neoplastic agents: current developments and promise of the PIH class of chelators. Curr Med Chem. Jun. 2003;10(12):1035-49.

Lui et al., The iron chelator, deferasirox, as a novel strategy for cancer treatment: oral activity against human lung tumor xenografts and molecular mechanism of action. Mol Pharmacol. Jan. 2013;83(1):179-90. doi: 10.1124/mol.112.081893. Epub Oct. 16, 2012.

MacPherson et al., Experimental production of diffuse colitis in rats. Digestion. 1978;17(2):135-50.

Malcovati, Impact of transfusion dependency and secondary iron overload on the survival of patients with myelodysplastic syndromes. Leuk Res. Dec. 2007;31 Suppl 3:S2-6.

Malluche et al., The Use of Deferoxamine in the Management of Aluminum Accumulation in Bone in Patients with Renal Failure. N Engl J Med. Jul. 19, 1984;311(3):140-4.

Millan et al., Biological signatures of brain damage associated with high serum ferritin levels in patients with acute ischemic stroke and thrombolytic treatment. Dis Markers. 2008;25(3):181-8.

Miller et al., Efficacy of orally administered amphipathic polyaminocarboxylic acid chelators for the removal of plutonium and americium: comparison with injected Zn-DTPA in the rat. Radiat Prot Dosimetry. 2006;118(4):412-20. Epub Dec. 6, 2005.

Mladenka et al., The fate of iron in the organism and its regulatory pathways. Acta Medica (Hradec Kralove). 2005;48(3-4):127-35.

Molina-Jijón et al., Deferoxamine pretreatment prevents Cr(VI)-induced nephrotoxicity and oxidant stress: Role of Cr(VI) chelation. Toxicol. 2012;291:93-101.

Moreau-Marquis et al., Tobramycin and FDA-approved iron chelators eliminate Pseudomonas aeruginosa biofilms on cystic fibrosis cells. Am J Respir Cell Mol Biol. Sep. 2009;41(3):305-13. doi: 10.1165/rcmb.2008-0299OC. Epub Jan. 23, 2009.

Mounsey et al., Chelators in the treatment of iron accumulation in Parkinson's disease. Int J Cell Biol. 2012;2012:983245. doi: 10.1155/2012/983245. Epub Jun. 13, 2012.

Naegeli et al., [Metabolites of Microorganisms.] Part 193. Ferrithiocin. Helv Chim Acta. 1980;63:1400-06. German.

Nash et al., Features of the thermodynamics of two-phase distribution reactions of americium(III) and europium(III) nitrates into solutions of 2,6-bis[(bis(2-ethylhexyl)phosphino)methyl]pyridine N,P,P'-trioxide. Inorg Chem. Nov. 4, 2002;41(22):5849-58.

Neu et al., Structural Characterization of a Plutonium(IV) Siderophore Complex: Single-Crystal Structure of Pu-Desferrioxamine E. Angew Chem Int Ed Engl. Apr. 2000;39(8):1442-1444.

Neufeld et al., A phase 2 study of the safety, tolerability, and pharmacodynamics of FBS0701, a novel oral iron chelator, in transfusional iron overload. Blood. Apr. 5, 2012;119(14):3263-8. doi: 10.1182/blood-2011-10-386268. Epub Jan. 17, 2012.

Nisbet-Brown et al., Effectiveness and safety of ICL670 in iron-loaded patients with thalassaemia: a randomised, double-blind, placebo-controlled, dose-escalation trial. Lancet. May 10, 2003;361(9369):1597-602.

O'Connell et al., The role of iron in ferritin- and haemosiderin-mediated lipid peroxidation in liposomes. Biochem J. Jul. 1, 1985;229(1):135-9.

Olivieri et al., Comparison of oral iron chelator L1 and desferrioxamine in iron-loaded patients. Lancet. 1990;336:1275-79.

Olivieri et al., Iron-chelating therapy and the treatment of thalassemia. Blood. Feb. 1, 1997;89(3):739-61.

Olivieri et al., Long-term safety and effectiveness of iron-chelation therapy with deferiprone for thalassemia major. N Engl J Med. Aug. 13, 1998;339(7):417-23.

Olivieri, Long-term therapy with deferiprone. Acta Haematol. 1996;95(1):37-48.

Olivieri, Progression of iron overload in sickle cell disease. Semin Hematol. Jan. 2001;38(1 Suppl 1):57-62.

Panter et al., Dextran-Coupled Deferoxamine Improves Outcome in a Murine Model of Head Injury. J Neurotrauma. 1992;9(1):47-53.

Paquet et al., Efficacy of 3,4,3-LI(1,2-HOPO) for decorporation of Pu, Am and U from rats injected intramuscularly with high-fired particles of MOX. Radiat Prot Dosimetry. 2003;105(1-4):521-5.

Pashalidis et al., Effective complex formation in the interaction of 1,2-dimethyl-3-hydroxypyrid-4-one (Deferiprone or L1) with uranium (VI). J Radioanal Nucl Chem. 1999;242:181-84.

Peters et al., Diagnosis and management of thalassaemia. BMJ. Jan. 25, 2012;344:e228. doi: 10.1136/bmj.e228.

(56) References Cited

OTHER PUBLICATIONS

Pietrangelo, Iron chelation beyond transfusion iron overload. Am J Hematol. Dec. 2007;82(12 Suppl):1142-6.
Pietrangelo, Mechanism of iron toxicity. In: Iron Chelation Therapy. Hershko, ed. 2002:19-43.
Pippard et al., Iron chelation using subcutaneous infusions of diethylene triamine penta-acetic acid (DTPA). Scand J Haematol. May 1986;36(5):466-72.
Pippard, Desferrioxamine-induced iron excretion in humans. Baillieres Clin Haematol. Apr. 1989;2(2):323-43.
Pippard, Iron overload and iron chelation therapy in thalassaemia and sickle cell haemoglobinopathies. Acta Haematol. 1987;78(2-3):206-11.
Platzer et al., Rate of drug metabolism in man measured by 14CO2-breath analysis. Eur J Clin Pharmacol. Dec. 1, 1978;14(4):293-9.
Ponka et al., Function and regulation of transferrin and ferritin. Semin Hematol. Jan. 1998;35(1):35-54.
Ponka et al., Mobilization of iron from reticulocytes. Identification of pyridoxal isonicotinoyl hydrazone as a new iron chelating agent. FEBS Lett. Jan. 15, 1979;97(2):317-21.
Potts et al., Traumatic injury to the immature brain: inflammation, oxidative injury, and iron-mediated damage as potential therapeutic targets. NeuroRx. Apr. 2006;3(2):143-53.
PubChem SID 241084044, Feb. 16, 2015.
Rao et al., Complexation of Thorium(IV) with Desmethyldesferrithiocin. Radiochim Acta. 2000;88:851-56.
Raymond et al., Coordination Chemistry and Microbial Iron Transport. Acc Chem Res. 1979;12:183-190.
Raymond et al., Enterobactin: an archetype for microbial iron transport. Proc Natl Acad Sci U S A. Apr. 1, 2003;100(7):3584-8. Epub Mar. 24, 2003.
Re et al., Antioxidant activity applying an improved ABTS radical cation decolorization assay. Free Radic Biol Med. May 1999;26(9-10):1231-7.
Richardson et al., Development of potential iron chelators for the treatment of Friedreich's ataxia: ligands that mobilize mitochondrial iron. Biochim Biophys Acta. May 31, 2001;1536(2-3):133-40.
Richardson, The controversial role of deferiprone in the treatment of thalassemia. J Lab Clin Med. May 2001;137(5):324-9.
Rienhoff et al., A phase 1 dose-escalation study: safety, tolerability, and pharmacokinetics of FBS0701, a novel oral iron chelator for the treatment of transfusional iron overload. Haematologica. Apr. 2011;96(4):521-5. doi: 10.3324/haematol.2010.034405. Epub Dec. 20, 2010.
Rosse, Metabolites of the pyrimidine amine preladenant as adenosine a2a receptor antagonists. ACS Med Chem Lett. Nov. 30, 2012;4(1):5-6. doi:10.1021/ml300397j. eCollection Jan. 10, 2013.
Saha et al., Microbial siderophores: a mini review. J Basic Microbiol. Apr. 2013;53(4):303-17. doi: 10.1002/jobm.201100552. Epub Jun. 26, 2012.
Saljooghi et al., Clinical evaluation of Deferasirox for removal of cadmium ions in rat. Biometals. 2010;23:707-12.
Saljooghi, Chelation of aluminum by combining deferasirox and deferiprone in rats. Toxicol Ind Health. 2012;28(8):740-5.
Santos et al., A cyclohexane-1, 2-diyldinitrilotetraacetate tetrahydroxamate derivative for actinide complexation: Synthesis and complexation studies. J Chem Soc Dalton Trans. 2000:4398-4402.
Seligman et al., Molecular Mechanisms of Iron Metabolism. The Molecular Basis of Blood Diseases. 1987;219-44.
Shibasaki et al. Seizaigaku butsuri yakuzaigaku. Tokyo: Hirokawashoten. Published May 1, 2012. Formulations. Physical pharmacy, 2nd edition. 259-66.
Shin et al., A novel trivalent cation chelator Feralex dissociates binding of aluminum and iron associated with hyperphosphorylated τ of Alzheimer's disease. Brain Res. 2003;961:139-46.
Shohami et al., Oxidative stress in closed-head injury: brain antioxidant capacity as an indicator of functional outcome. J Cereb Blood Flow Metab. 1997;17(10):1007-1019. doi:10.1097/00004647-199710000-00002.
Short et al., Safety Evaluation of Ocular Drug Delivery Formulations: Techniques and Practical Considerations. Toxicologic Pathology. Dec. 31, 2008;36(1):49-62.
Stahel et al., Iron chelators: in vitro inhibitory effect on the liver stage of rodent and human malaria. Am J Trop Med Hyg. Sep. 1988;39(3):236-40.
Stradling et al., Recent developments in the decorpoartion of plutonium, americium and thorium. Radiat Prot Dosimetry. 1998;79:445-48.
Streiff et al., Phase 1 study of N1-N11-diethylnorspermine (DENSPM) administered TID for 6 days in patients with advanced malignancies. Invest New Drugs. 2001;19(1):29-39.
Taetle et al., Combination iron depletion therapy. J Natl Cancer Inst. Aug. 16, 1989;81(16):1229-35.
Theil et al., Ferritin Mineralization: Ferroxidation and Beyond. J Inorg Biochem. 1997;67:30. Abstract B13.
Thomas et al., Ferritin and superoxide-dependent lipid peroxidation. J Biol Chem. Mar. 25, 1985;260(6):3275-80.
Uhlir et al., Specific sequestering agents for the actinides. 21. Synthesis and initial biological testing of octadentate mixed catecholate-hydroxypyridinonate ligands. J Med Chem. Feb. 19, 1993;36(4):504-9.
Vichinsky, Current issues with blood transfusions in sickle cell disease. Semin Hematol. Jan. 2001;38(1 Suppl 1):14-22.
Wen et al., High serum iron is associated with increased cancer risk. Cancer Res. Nov. 15, 2014;74(22):6589-97. doi: 10.1158/0008-5472.CAN-14-0360. Epub Sep. 16, 2014.
Whisenhunt et al., Specific Sequestering Agents for the Actinides. 29. Stability of the Thorium(IV) Complexes of Desferrioxamine B (DFO) and Three Octadentate Catecholate or Hydroxypyridinonate DFO Derivatives: DFOMTA, DFOCAMC, and DFO-1,2-HOPO. Comparative Stability of the Plutonium(IV) DFOMTA Complex(1). Inorg Chem. Jul. 3, 1996;35(14):4128-4136.
White et al., Brain injury and repair mechanisms: the potential for pharmacologic therapy in closed-head trauma. Ann Emerg Med. 1993;22(6):970-979. doi:10.1016/s0196-0644(05)82737-4.
White et al., The effect of chelating agents on cellular iron metabolism. Clin Sci Mol Med. Mar. 1976;50(3):145-52.
White et al., The effect of chelating agents on iron mobilization in Chang cell cultures. Blood. Dec. 1976;48(6):923-9.
Whittington et al., Review article: haemochromatosis. Aliment Pharmacol Ther. Dec. 2002;16(12):1963-75.
Wojcik et al., Natural history of C282Y homozygotes for hemochromatosis. Can J Gastroenterol. May 2002;16(5):297-302.
Wolfe et al., A non-human primate model for the study of oral iron chelators. Br J Haematol. Jul. 1989;72(3):456-61.
Wolff et al., A Phase II study of the polyamine analog N1,N11-diethylnorspermine (DENSpm) daily for five days every 21 days in patients with previously treated metastatic breast cancer. Clin Cancer Res. Dec. 1, 2003;9(16 Pt 1):5922-8.
Wong et al., The Friedreich's ataxia mutation confers cellular sensitivity to oxidant stress which is rescued by chelators of iron and calcium and inhibitors of apoptosis. Hum Mol Genet. Mar. 1999;8(3):425-30.
Wood et al., The metabolism of iron-dextran given as a total-dose infusion to iron deficient Jamaican subjects. Br J Haematol. Feb. 1968;14(2):119-29.
Yacobovich et al., Acquired proximal renal tubular dysfunction in β-thalassemia patients treated with deferasirox. J Pediatr Hematol Oncol. Oct. 2010;32(7):564-7. doi: 10.1097/MPH.0b013e3181ec0c38.
Yamada et al., Role of neutrophil-derived oxidants in the pathogenesis of intestinal inflammation. Klin Wochenschr. Dec. 15, 1991;69(21-23):988-94.
Zacharski et al., Reduction of iron stores and cardiovascular outcomes in patients with peripheral arterial disease: a randomized controlled trial. JAMA. Feb. 14, 2007;297(6):603-10.
Zaman et al., Protection from oxidative stress-induced apoptosis in cortical neuronal cultures by iron chelators is associated with enhanced DNA binding of hypoxia-inducible factor-1 and ATF-1/CREB and increased expression of glycolytic enzymes, p21(waf1/cip1), and erythropoietin. J Neurosci. Nov. 15, 1999;19(22):9821-30.

(56) References Cited

OTHER PUBLICATIONS

Zecca et al., Neuromelanin can protect against iron-mediated oxidative damage in system modeling iron overload of brain aging and Parkinson's disease. J Neurochem. Aug. 2008;106(4):1866-75. Epub Jul. 4, 2008.

Zeng et al., Identification of cytochrome P4503A as the major enzyme sub-family responsible for the metabolism of 22,23-dihydro-13-O-[(2-methoxyethoxy)methyl]-avermectin B1 aglycone by rat liver microsomes. Xenobiotica. Oct. 1997;27(10):985-94.

Zhao et al., Specific method for determination of OSI-774 and its metabolite OSI-420 in human plasma by using liquid chromatography-tandem mass spectrometry. J Chromatogr B Analyt Technol Biomed Life Sci. Aug. 15, 2003;793(2):413-20.

Zurlo et al., Survival and causes of death in thalassaemia major. Lancet. Jul. 1, 1989;2(8653):27-30.

Haimovici R, D'Amico DJ, Gragoudas ES, Sokol S, Deferoxamine Retinopathy Study Group. The expanded clinical spectrum of deferoxamine retinopathy. Ophthalmology. Jan. 1, 2002;109(1):164-71.

Gaudana R, Ananthula HK, Parenky A, Mitra AK. Ocular drug delivery. The AAPS journal. Sep. 2010;12:348-60.

| Animal | Compound concentration in rat plasma (µM) | Compound concentration in rat eye (nmol/g wet weight of rat eye) |
| --- | --- | --- |
| Rat #9 | 195.75 | 13.78 |
| Rat #10 | 173.85 | 12.85 |
| Rat #11 | 186.90 | 20.80 |
| Rat #13 | 195.15 | 10.88 |
| Rat #14 | 171.60 | 15.79 |
| Rat #21 | 288.45 | 23.04 |
| Rat #22 | 159.00 | 10.48 |
| Rat #23 | 240.15 | 17.93 |
| Rat #24 | 301.20 | 28.39 |
| Rat #25 | 279.30 | 19.61 |
| Rat #26 | 204.90 | 15.16 |
| | | |
| AVG | 217.84 | 17.16 |
| STD | 50.87 | 5.48 |

| Animal | Compound concentration in rat plasma (μM) | Compound concentration in rat eye (nmol/g wet weight of rat eye) |
|---|---|---|
| Rat #15 | 238.95 | 22.32 |
| Rat #16 | 192.30 | 19.87 |
| Rat #17 | 218.70 | 24.17 |
| Rat #18 | 222.90 | 21.99 |
| Rat #19 | 226.80 | 31.35 |
| Rat #20 | 208.95 | 35.05 |
| AVG | 218.10 | 25.79 |
| STD | 16.02 | 6.01 |

USES OF 4'-DESFERRITHIOCIN ANALOGS

RELATED APPLICATIONS

The present application is a continuation of and claims priority under 35 U.S.C. § 120 to U.S. application Ser. No. 15/424,557, filed Feb. 3, 2017, which is a continuation of and claims priority under 35 U.S.C. § 120 to U.S. application Ser. No. 14/363,886, filed Jun. 9, 2014, which is a national stage filing under 35 U.S.C. § 371 of international PCT application, PCT/US2012/069795, filed Dec. 14, 2012, which claims priority under 35 U.S.C. § 119(e) to U.S. provisional patent application, U.S. Ser. No. 61/576,920, filed Dec. 16, 2011, each of which is incorporated herein by reference.

GOVERNMENT SUPPORT

This invention was made with U.S. Government support under grant number R37DK049108 awarded by National Institute of Diabetes and Digestive and Kidney Diseases of the National Institutes of Health. The U.S. Government has certain rights in the invention.

BACKGROUND OF THE INVENTION

Iron metabolism in primates is characterized by a highly efficient recycling process. Brittenham, "Disorders of Iron Metabolism: Iron Deficiency and Overload" In *Hematology: Basic Principles and Practice;* 3rd ed.; Hoffman et al., Eds.; Churchill Livingstone: New York, 2000; 397-428. Consequently, there is no specific mechanism for eliminating this transition metal. Because of the lack of an iron clearance mechanism, the introduction of "excess iron" into this closed metabolic loop often leads to chronic iron overload and can ultimately lead to biological damage (e.g., peroxidative tissue damage). There are a number of ways in which excess iron is introduced, including a high-iron diet, acute iron ingestion, or malabsorption of the metal. Conrad et al. "Iron Absorption and Transport" *Am. J. Med. Sci.* 1999, 318:213-229; Lieu et al. "The Roles of Iron in Health and Disease" *Mol. Aspects Med.* 2001, 22:1-87. In each of these situations, a subject can be treated by phlebotomy to reduce iron levels. However, for iron-overload syndromes resulting from chronic transfusion therapy, e.g., aplastic anemia and thalassemia (Olivieri et al. "Iron-chelating Therapy and the Treatment of Thalassemia" Blood 1997, 89:739-761; Vichinsky, "Current Issues with Blood Transfusions in Sickle Cell Disease" *Semin. Hematol.* 2001, 38:14-22; Kersten et al. "Long-Term Treatment of Transfusional Iron Overload with the Oral Iron Chelator Deferiprone (L1): A Dutch Multicenter Trial" *Ann. Hematol.* 1996, 73:247-252), phlebotomy is not an option. In these secondary iron overload syndromes, the origin of the excess iron is the transfused red blood cells. Since removing the red blood cells to remedy the iron overload would be counterproductive, an alternative method of removing iron is chelation therapy.

Although considerable effort has been invested in the development of new therapeutics for managing iron overload resulting from thalassemia, particularly therapeutics that can be administered orally, desferrioxamine B, a hexacoordinate hydroxamate iron chelator produced by *Streptomyces pilosus*, is still the drug of choice. However, desferrioxamine B is not ideal for chelation therapy because iron is removed with a low efficiency. In addition, the oral activity of desferrioxamine B is marginal, thereby requiring parenteral administration, which can result in poor patient compliance, particularly for patients in need of long-term chelation therapy.

In recent years, a substantial number of synthetic metal chelators have been studied as potential orally active therapeutic agents, e.g., pyridoxal isonicotinoyl hydrazone (PIH), hydroxypyridones and N, N'-bis-(2-hydroxybenzylethylenediamine)-N, N'-diacetic acid (HBED); however, these synthetic chelators have not yet demonstrated the desired properties for an ideal metal chelator therapeutic (e.g., effective chelation, suitable oral activity, and acceptable toxicity). Siderophores including enterobactin and rhodotorulic acid have also been studied. However, both enterobactin and rhodotorulic acid exhibit unacceptable toxicity, and neither demonstrated measurable oral activity. In general, although a large number of siderophores and synthetic iron chelators have been developed, most have been abandoned because their properties are not suitable for use in treating chronic iron overload.

The thiazoline-based siderophore desferrithiocin, isolated from *Streptomyces antibioticus*, has also been studied. Desferrithiocin analogs, including desazadesferrithiocin and desferrithiocin polyether analogs, have been investigated as orally active therapeutic agents for treating iron overload. The work on such analogs is described in International PCT Applications, PCT/US99/19691, filed Aug. 31, 1999; PCT/US2003/028304, filed Sep. 9, 2003; PCT/US2006/010945, filed Mar. 22, 2006; and PCT/US2008/003433, filed Mar. 14, 2008; each of which is incorporated herein by reference. These analogs have been found useful in treating diseases associated with global iron overload, such as that resulting from chronic transfusion therapy used to treat thalassemia and other transfusion-dependent anemias. Phase 2 clinical trials studying the safety and efficacy of a desferrithiocin analog in iron overload patients are ongoing.

Although not typically associated with iron overload, diseases including macular degeneration, stroke, irritable bowel disease, closed head injury, and reperfusion injury are all diseases associated with significant morbidity and mortality. For instance, macular degeneration results in the loss of central vision and is a major cause of blindness and visual impairment in older adults. Subjects with macular degeneration frequently cannot read or recognize faces due to their visual impairment. Stroke is caused by a lack of blood flow to an area of the brain and depending on the area of the brain affected can result in the inability to move limbs on one side of the body or can affect speech or vision. Reperfusion injury is due to oxidative stress in ischemic tissue after blood flow has been restored. Irritable bowel disease (IBD) is a functional bowel disease characterized by abdominal pain and discomfort, bloating, diarrhea, and/or constipation in the absence of any detectable cause. Although IBD does not lead to more serious problems in most patients, it is a source of chronic pain and fatigue for patients who suffer with this condition. And finally closed head injury is the leading cause of death in children under 4 years of age and is the most common cause of physical disability and cognitive impairment in young people. All of these diseases need better treatments including new approaches to their treatment.

SUMMARY OF THE INVENTION

The present invention stems from the recognition that the pathogenesis of various diseases, including macular degeneration, closed head injury, irritable bowel disease (IBD), stroke, reperfusion injury, and other diseases and conditions, involves free iron and the generation of reactive oxygen species (ROS), including superoxide anion, hydrogen peroxide, hypochlorous acid, and hydroxyl radicals, and other longer lived, free radicals. Such radicals are now realized to be important contributors to many diseases including macular degeneration, head injury, IBD, stroke, and reperfusion injury. As appreciated in the art, free iron contributes to the formation of reactive oxygen species. For example, $Fe^{+2}$ ions in biological systems react with oxygen species to produce highly reactive hydroxyl radicals via the Fenton reaction (see scheme below). The hydroxyl radical is a highly effective oxidizing agent, reacting at a diffusion-controlled rate with most organic species, such as nucleic acids, proteins, and lipids. Furthermore, superoxide anions or a biological reductant (e.g., ascorbic acid) can reduce the resulting $Fe^{+3}$ ion back to $Fe^{+2}$ for continued peroxide reduction, thus a problematic cycle.

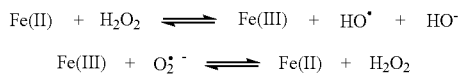

Therefore, diseases or conditions that lead to bleeding and/or an inflammatory response involve the possibility that reactive oxygen species will come in contact with $Fe^{+2}$ ions to produce highly reactive and damaging hydroxyl radicals. That is, the iron released from red blood cells react with oxygen species produced by inflammatory cells such as neutrophils to produce hydroxyl radicals that cause cell and tissue injury. The solution, therefore, is the same for conditions of focal iron overload (e.g., closed head injury, hemorrhagic stroke, IBD) as it is for global iron overload—chelation and removal of the unmanaged iron.

Various desferrithiocin analogs, including desferrithiocin polyether analogs, have been developed that effectively chelate and remove iron from biological systems. See International PCT Applications, PCT/US99/19691, filed Aug. 31, 1999; PCT/US2003/028304, filed Sep. 9, 2003; PCT/US2006/010945, filed Mar. 22, 2006; PCT/US2008/003433, filed Mar. 14, 2008; PCT/US2010/002336, filed Aug. 25, 2010; each of which is incorporated herein by reference. Therefore, the present invention applies the use of these analogs, which have been previously only suggested for use in the treatment of global metal overload, to diseases and conditions associated with focal iron overload, such as, but not limited to, macular degeneration, stroke, IBD, closed head injury, and reperfusion injury. In certain embodiments, the desferrithiocin analog useful in the present invention is of Formula (I):

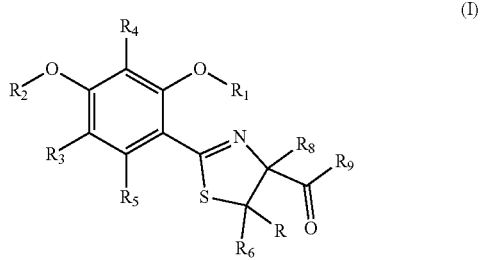

wherein $R_1$-$R_9$ are as defined here. In certain embodiments, desferrithiocin analogs with a poly ether moiety at the 4'-position of the phenyl ring are used in the present invention (i.e., $R_2$ is a poly ether moiety). Such analogs have been found to be useful in treating diseases or conditions associated with focal iron overload, for example, where iron has been introduced into an organ, tissue, or space by bleeding or through an inflammatory response. In certain embodiments, such analogs have been found in the cerebral spinal fluid (CSF) and therefore may be useful in treating neurological diseases such as closed head injury or stroke. In certain embodiments, such analogs have been found to penetrate into the eye and may be useful in treating ophthalmologic diseases such as macular degeneration. All of these diseases are associated with free radical damage resulting from unmanaged or free iron in the respective tissue or organ. Therefore, the chelation and removal of the free iron in these tissues and organs would be effective in preventing or treating each of these diseases.

Based on this recognition the present invention provides methods of treating and preventing diseases and conditions associated with focal iron overload and pharmaceutical compositions for use in treating such diseases and conditions. The invention provides new uses for previously known compounds in the treatment of diseases and conditions associated with focal iron overload. The invention also provides kits including compounds and compositions found useful in treatment of such disease and conditions.

In one aspect, the invention provides methods of preventing or treating macular degeneration by administering to a subject an effective amount of a compound of Formula (I) to prevent or treat macular degeneration. Compounds of Formula (I) have been found to get into the eye and chelate and remove iron that is thought to contribute to the generation of reactive oxygen species in the eye that cause biological injury. Such reactive oxygen species are particularly detrimental in the retina of the eye. The present invention also provides pharmaceutical compositions suitable for ocular administration and uses of the compounds of Formula (I) and compositions thereof for the treatment of macular degeneration. In certain embodiments, the pharmaceutical composition for ocular administration is in the form of an eyedrop. The compound of Formula (I) or a composition thereof may also be administered systemically for the treatment of macular degeneration.

In another aspect, the invention provides methods of removing iron from tissues or organs that have been bled into or otherwise have focal iron overload. For example, methods for the treatment of head injury, including closed head injury, are provided. Closed head injuries that may be treated by the inventive methods and compositions may result from any number of causes including falls, blasts, sports injuries, accidents including vehicular accidents, and assaults. In certain embodiments, the inventive method comprises administering to a subject an effective amount of a compound of Formula (I) to sequester iron resulting from a hemorrhage or vascular compromise in the head. In certain embodiments, the subject has suffered from a closed head injury. In other embodiments, the subject has suffered from or is at risk of suffering from a stroke (e.g., a hemorrhagic stroke). The present invention also provides pharmaceutical compositions for the treatment of head injury and uses of the compounds of Formula (I) and compositions thereof for the treatment of head injury. In certain embodiments for the treatment of head injury, the compound of Formula (I) or a composition thereof is administered systemically (e.g., orally or parenterally).

In another aspect, the invention provides methods for the treatment of stroke, particularly hemorrhagic stroke. Such methods include administering a compound of Formula (I) to a subject at risk of having a stroke or having had a stroke.

In certain embodiments, the method comprises administering to a subject who has had or is at risk of having a stroke an effective amount of a compound of Formula (I). Without wishing to be bound by a particular theory, the administered compound is thought to sequester iron resulting from hemorrhage or vascular compromise thereby preventing or at least lessening tissue damage caused by reactive oxygen species. Such reactive oxygen species may be generated by free iron ions resulting from the bleed in the brain. In certain embodiments, the subject has suffered from a hemorrhagic stroke. In other embodiments, the subject is at risk of having a hemorrhagic stroke. The present invention also provides pharmaceutical compositions for the treatment of stroke and uses of the compounds of Formula (I) and compositions thereof for the treatment of stroke. In certain embodiments for the treatment of stroke, the compound of Formula (I) or a composition thereof is administered systemically (e.g., orally or parenterally).

In another aspect, the invention provides methods for preventing or lessening reperfusion injury. Reperfusion injury is caused by reactive oxygen species that are generated when the blood supply returns to a tissue after a period of ischemia. Compounds of Formula (I) or compositions thereof are administered to a subject at risk of reperfusion injury to prevent the formation of reactive oxygen species or inactivate free radical species. Ischemia may result from a number of causes including stroke, myocardial infarction, infarction of other tissues or organs, surgery (e.g., cardiac surgery), and organ donation and transplantation. The present invention also provides pharmaceutical compositions for the prevention and treatment of reperfusion injury as well as the uses of compounds of Formula (I) and compositions thereof for the prevention and treatment of reperfusion injury. The compounds of Formula (I) or compositions thereof may be administered locally or systemically in the prevention or treatment of reperfusion injury.

In yet another aspect, the present invention provides methods of treating irritable bowel disease (IBD). Reactive oxygen species have been found important in the pathogenesis of IBD; therefore, as described above for the treatment of reperfusion injury, any compound, composition, or treatment that chelates and removes iron and/or quenches free radicals would be useful in the treatment of IBD. In certain embodiments, the method comprises administering to a subject an effective amount of a compound of Formula (I) or a composition thereof to treat IBD. The present invention also provides pharmaceutical compositions for the treatment of IBD and the uses of the compounds of Formula (I) and compositions thereof for the treatment of IBD. The compounds of Formula (I) or compositions thereof may be administered locally (e.g., rectally) or systemically in the treatment of IBD.

The present invention also provides kits with the compound of Formula (I) or compositions thereof for use in the treatment of macular degeneration, head injury (e.g., closed head injury), stroke (e.g., hemorrhagic stroke), reperfusion injury, and IBD. Such kits may include one or more unit dosage forms of the compound or composition to be administered to a subject. In certain embodiments, the kit may include enough unit dosage forms for a course of treatment or for a particular time period (e.g., a week, 10 days, 14 days, a month). The kits may also include packaging information describing the use or prescribing information for the subject or a health care professional. Such information may be required by a regulatory agency such as the U.S. Food and Drug Administration (FDA). The kit may also optionally include a device for administration of the compound or composition, for example, a dropper for ocular administration or a syringe for parenteral administration.

The details of one or more embodiments of the invention are set forth in the accompanying Detailed Description, Examples, Claims, and Figures. Other features, objects, and advantages of the invention will be apparent from the description and claims.

The references, web pages, scientific journal articles, patent applications, and issued patents cited in this application are incorporated herein by reference.

Definitions

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987.

The compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention.

Where an isomer/enantiomer is preferred, it may, in some embodiments, be provided substantially free of the corresponding enantiomer, and may also be referred to as "optically enriched" or "enantiomerically enriched." "Optically enriched" and "enantiomerically enriched," as used herein, means that a provided compound is made up of a significantly greater proportion of one enantiomer. In certain embodiments, a compound of the present invention is made up of at least about 70% by weight of a preferred enantiomer. In certain embodiments, a compound of the present invention is made up of at least about 80% by weight of a preferred enantiomer. In certain embodiments, a compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); Wilen, *Tables of Resolving Agents and Optical Resolutions* p. 268 (E. L. Eliel, Ed., Univ. of Notre Dame Press, Notre Dame, Ind. 1972).

Unless otherwise stated, structures depicted herein are also meant to include compounds that differ only in the presence of one or more isotopically enriched atoms. For example, compounds having the depicted structures that differ only in the replacement of hydrogen by deuterium or tritium, or the replacement of a carbon by $^{13}C$ or $^{14}C$ are within the scope of this invention. Such compounds are useful, for example, as analytical tools, as probes in biological assays, or as therapeutic agents in accordance with the present invention.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The terms "purified," "substantially purified," and "isolated" as used herein refer to a compound useful in the present invention being free of other, dissimilar compounds with which the compound is normally associated in its natural state, so that the compound comprises at least 0.5%, 1%, 5%, 10%, 20%, 50%, 75%, 80%, 85%, 90%, 95%, 96%, 97%, 98%, 99%, 99.5%, 99.9% of the mass, by weight, of a given sample or composition. In one embodiment, these terms refer to the compound comprising at least 95%, 98%, 99%, or 99.9% of the mass, by weight, of a given sample or composition.

The term "acyl," as used herein, refers to a group having the general formula —C(=O)$R^{X1}$, —C(=O)O$R^{X1}$, —C(=O)—O—C(=O)$R^{X1}$, —C(=O)S$R^{X1}$, —C(=O)N($R^{X1}$)$_2$, —C(=S)$R^{X1}$, —C(=S)N($R^{X1}$)$_2$, and —C(=S)S($R^{X1}$), —C(=N$R^{X1}$)$R^{X1}$, —C(=N$R^{X1}$)O$R^{X1}$, —C(=N$R^{X1}$)S$R^{X1}$, and —C(=N$R^{X1}$)N($R^{X1}$)$_2$, wherein $R^{X1}$ is hydrogen; halogen; substituted or unsubstituted hydroxyl; substituted or unsubstituted thiol; substituted or unsubstituted amino; substituted or unsubstituted acyl; cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "acyloxy" refers to a "substituted hydroxyl" of the formula (—OR$^t$), wherein R$^t$ is an optionally substituted acyl group, as defined herein, and the oxygen moiety is directly attached to the parent molecule.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkyl," as used herein, refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-20 carbon atoms. In another embodiment, the alkyl group employed contains 1-15 carbon atoms. In another embodiment, the alkyl group employed contains 1-10 carbon atoms. In another embodiment, the alkyl group employed contains 1-8 carbon atoms. In another embodiment, the alkyl group employed contains 1-5 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substituents. Alkyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkenyl," as used herein, denotes a monovalent group derived from a straight- or branched-chain hydrocarbon moiety having at least one carbon-carbon double bond by the removal of a single hydrogen atom. In certain embodiments, the alkenyl group employed in the invention contains 2-20 carbon atoms. In some embodiments, the alkenyl group employed in the invention contains 2-15 carbon atoms. In another embodiment, the alkenyl group employed contains 2-10 carbon atoms. In still other embodiments, the alkenyl group contains 2-8 carbon atoms. In yet other embodiments, the alkenyl group contains 2-5 carbons. Alkenyl groups include, for example, ethenyl, propenyl, butenyl, l-methyl-2-buten-1-yl, and the like, which may bear one or more substituents. Alkenyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkynyl," as used herein, refers to a monovalent group derived from a straight- or branched-chain hydrocarbon having at least one carbon-carbon triple bond by the removal of a single hydrogen atom. In certain embodiments, the alkynyl group employed in the invention contains 2-20 carbon atoms. In some embodiments, the alkynyl group employed in the invention contains 2-15 carbon atoms. In another embodiment, the alkynyl group employed contains 2-10 carbon atoms. In still other embodiments, the alkynyl group contains 2-8 carbon atoms. In still other embodiments, the alkynyl group contains 2-5 carbon atoms. Representative alkynyl groups include, but are not limited to, ethynyl, 2-propynyl (propargyl), 1-propynyl, and the like, which may bear one or more substituents. Alkynyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_6$ m aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_6$ m aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_6$ m aryl, 3-10 membered heterocyclyl, 5-10 membered heteroaryl; or two geminal $R^{gg}$ substituents can be joined to form =O or =S; wherein X is a counterion.

The term "amino," as used herein, refers to a group of the formula (—NH$_2$). A "substituted amino" refers either to a mono-substituted amine (—NHR$^h$) of a disubstituted amine (—NR$^h_2$), wherein the R$^h$ substituent is any substituent as described herein that results in the formation of a stable moiety (e.g., a suitable amino protecting group; aliphatic, alkyl, alkenyl, alkynyl, heteroaliphatic, heterocyclic, aryl, heteroaryl, acyl, amino, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). In certain embodiments, the R$^h$ substituents of the di-substituted amino group (—NR$^h_2$) form a 5- to 6-membered heterocyclic ring.

The term "alkoxy" refers to a "substituted hydroxyl" of the formula (—OR$^i$), wherein R$^i$ is an optionally substituted alkyl group as defined herein, and the oxygen moiety is directly attached to the parent molecule.

The term "alkylthioxy" refers to a "substituted thiol" of the formula (—SR$^r$), wherein R$^r$ is an optionally substituted alkyl group as defined herein, and the sulfur moiety is directly attached to the parent molecule.

The term "alkylamino" refers to a "substituted amino" of the formula (—NR$^h_2$), wherein R$^h$ is, independently, a hydrogen or an optionally substituted alkyl group as defined herein, and the nitrogen moiety is directly attached to the parent molecule.

The term "aryl," as used herein, refer to stable aromatic mono- or polycyclic ring system having 3-20 ring atoms, of which all the ring atoms are carbon, and which may be substituted or unsubstituted. In certain embodiments of the present invention, "aryl" refers to a mono, bi, or tricyclic C$_4$-C$_{20}$ aromatic ring system having one, two, or three aromatic rings which include, but not limited to, phenyl, biphenyl, naphthyl, and the like, which may bear one or more substituents. Aryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "arylalkyl," as used herein, refers to an aryl substituted alkyl group, wherein the terms "aryl" and "alkyl" are defined herein, and wherein the aryl group is attached to the alkyl group, which in turn is attached to the parent molecule. An exemplary arylalkyl group is benzyl.

The term "aryloxy" refers to a "substituted hydroxyl" of the formula (—OR$^i$), wherein R$^i$ is an optionally substituted aryl group as defined herein, and the oxygen moiety is directly attached to the parent molecule.

The term "arylamino," refers to a "substituted amino" of the formula (—NR$^h_2$), wherein R$^h$ is, independently, a hydrogen or an optionally substituted aryl group as defined herein, and the nitrogen moiety is directly attached to the parent molecule.

The term "arylthioxy" refers to a "substituted thiol" of the formula (—SR$^r$), wherein R$^r$ is an optionally substituted aryl group as defined herein, and the sulfur moiety is directly attached to the parent molecule.

The term "azido," as used herein, refers to a group of the formula (—N$_3$).

The term "cyano," as used herein, refers to a group of the formula (—CN).

The terms "halo" and "halogen" as used herein refer to an atom selected from fluorine (fluoro, —F), chlorine (chloro, —Cl), bromine (bromo, —Br), and iodine (iodo, —I).

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl", "heteroalkynyl", and the like. Furthermore, as used herein, the terms "heteroalkyl", "heteroalkenyl", "heteroalkynyl", and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkyl," as used herein, refers to an alkyl moiety, as defined herein, which contain one or more oxygen, sulfur, nitrogen, phosphorus, or silicon atoms, e.g., in place of carbon atoms.

The term "heteroalkenyl," as used herein, refers to an alkenyl moiety, as defined herein, which contain one or more oxygen, sulfur, nitrogen, phosphorus, or silicon atoms, e.g., in place of carbon atoms.

The term "heteroalkynyl," as used herein, refers to an alkynyl moiety, as defined herein, which contain one or more oxygen, sulfur, nitrogen, phosphorus, or silicon atoms, e.g., in place of carbon atoms.

The term "heteroalkylamino" refers to a "substituted amino" of the formula (—NR$^h_2$), wherein R$^h$ is, independently, a hydrogen or an optionally substituted heteroalkyl group, as defined herein, and the nitrogen moiety is directly attached to the parent molecule.

The term "heteroalkyloxy" refers to a "substituted hydroxyl" of the formula (—OR$^i$), wherein R$^i$ is an optionally substituted heteroalkyl group, as defined herein, and the oxygen moiety is directly attached to the parent molecule.

The term "heteroalkylthioxy" refers to a "substituted thiol" of the formula (—SR$^r$), wherein R$^r$ is an optionally substituted heteroalkyl group, as defined herein, and the sulfur moiety is directly attached to the parent molecule.

The term "heterocyclic," "heterocycles," or "heterocyclyl," as used herein, refers to a cyclic heteroaliphatic group. A heterocyclic group refers to a non-aromatic, partially unsaturated or fully saturated, 3- to 12-membered ring system, which includes single rings of 3 to 8 atoms in size, and bi- and tri-cyclic ring systems which may include aromatic five- or six-membered aryl or heteroaryl groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocyclyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Exemplary heterocycles include azacyclopropanyl, azacyclobutanyl, 1,3-diazatidinyl, piperidinyl, piperazinyl, azocanyl, thiaranyl, thietanyl, tetrahydrothiophenyl, dithiolanyl, thiacyclohexanyl, oxiranyl, oxetanyl, tetrahydrofuranyl, tetrahydropuranyl, dioxanyl, oxathiolanyl, morpholinyl, thioxanyl, tetrahydronaphthyl, and the like, which may bear one or more substituents. Substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroaryl," as used herein, refer to stable aromatic mono- or polycyclic ring system having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include, but are not limited to pyrrolyl, pyrazolyl, imidazolyl, pyridinyl, pyrimidinyl, pyrazinyl, pyridazinyl, triazinyl, tetrazinyl, pyyrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl, oxadiaziolyl, and the like, which may bear one or more substituents. Heteroaryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroarylene," as used herein, refers to a biradical derived from an heteroaryl group, as defined herein, by removal of two hydrogen atoms. Heteroarylene groups may be substituted or unsubstituted. Additionally, heteroarylene groups may be incorporated as a linker group into an alkylene, alkenylene, alkynylene, heteroalkylene, heteroalkenylene, or heteroalkynylene group, as defined herein. Heteroarylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroarylamino" refers to a "substituted amino" of the (—NR$^h_2$), wherein R$^h$ is, independently, a hydrogen or an optionally substituted heteroaryl group, as defined herein, and the nitrogen moiety is directly attached to the parent molecule.

The term "heteroaryloxy" refers to a "substituted hydroxyl" of the formula (—OR$^i$), wherein R$^i$ is an optionally substituted heteroaryl group, as defined herein, and the oxygen moiety is directly attached to the parent molecule.

The term "heteroarylthioxy" refers to a "substituted thiol" of the formula (—SR$^r$), wherein R$^r$ is an optionally substituted heteroaryl group, as defined herein, and the sulfur moiety is directly attached to the parent molecule.

The term "hydroxy," or "hydroxyl," as used herein, refers to a group of the formula (—OH). A "substituted hydroxyl" refers to a group of the formula (—OR$^i$), wherein R$^i$ can be any substituent which results in a stable moiety (e.g., a suitable hydroxyl protecting group; aliphatic, alkyl, alkenyl, alkynyl, heteroaliphatic, heterocyclic, aryl, heteroaryl, acyl, nitro, alkylaryl, arylalkyl, and the like, each of which may or may not be further substituted).

The term "imino," as used herein, refers to a group of the formula (=NR$^r$), wherein R$^r$ corresponds to hydrogen or any substituent as described herein, that results in the formation of a stable moiety (for example, a suitable amino protecting group; aliphatic, alkyl, alkenyl, alkynyl, heteroaliphatic, heterocyclic, aryl, heteroaryl, acyl, amino, hydroxyl, alkylaryl, arylalkyl, and the like, each of which may or may not be further substituted). In certain embodiments, imino refers to =NH wherein R$^r$ is hydrogen.

The term "isocyano," as used herein, refers to a group of the formula (—NC).

The term "nitro," as used herein, refers to a group of the formula (—NO$_2$).

The term "oxo," as used herein, refers to a group of the formula (=O).

The term "stable moiety," as used herein, preferably refers to a moiety which possess stability sufficient to allow manufacture, and which maintains its integrity for a sufficient period of time to be useful for the purposes detailed herein.

A "protecting group," as used herein, is well known in the art and include those described in detail in *Greene's Protective Groups in Organic Synthesis*, P. G. M. Wuts and T. W. Greene, 4$^{th}$ edition, Wiley-Interscience, 2006, the entirety of which is incorporated herein by reference. Suitable amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5- chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), 0-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

A "suitable hydroxyl protecting group" as used herein, is well known in the art and includes those described in detail in Greene (1999). Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

The term "subject," as used herein, refers to any animal. In certain embodiments, the subject is a mammal. In certain embodiments, the term "subject", as used herein, refers to a human (e.g., a man, a woman, or a child). The human may be of either sex and may be at any stage of development. In certain embodiments, the subject has been diagnosed with the condition or disease to be treated (e.g., macular degeneration, stroke, IBD, closed head injury). In other embodiments, the subject is at risk of developing the condition or disease. In certain embodiments, the subject is an experimental animal (e.g., mouse, rat, dog, primate). The experimental animal may be genetically engineered. In certain embodiments, the subject is a domesticated animal (e.g., dog, cat, bird, horse, cow, goat, sheep).

The terms "administer," "administering," or "administration," as used herein refers to implanting, absorbing, ingesting, injecting, or inhaling a compound of Formula (I) or a pharmaceutical composition thereof.

As used herein, the terms "treatment," "treat," and "treating" refer to reversing, alleviating, delaying the onset of, or inhibiting the progress of a disease or disorder, or one or more signs or symptoms thereof, described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example to delay or prevent recurrence.

The terms "effective amount" and "therapeutically effective amount," as used herein, refer to the amount or concentration of an inventive compound, that, when administered to a subject, is effective to at least partially treat a condition from which the subject is suffering (e.g., chronic inflammatory disease, autoimmune disease, dry eye syndrome, fibrosis, scar formation, angiogenesis, viral infection, malaria, ischemic damage, transplant and implant rejection, neurodegenerative disease, or a cosmetic indication).

The term "focal iron overload" refers to any disease or condition that involves the accumulation of unmanaged iron in a tissue or organ. Focal iron overload typically involves less than the subject's whole body but may involve more than one organ or tissue. Unmanaged iron in any tissue or organ is typically undesired and can be the focus of the treatments of the present invention. The treatment may involve the removal of as much iron as possible from the tissue or organ or may only involve the removal of excess iron. Examples of disease and conditions associated with focal iron overload include, but are not limited to, macular degeneration, IBD, reperfusion injury, stroke including hemorrhagic stroke, and closed head injury; however, any disease or condition of focal iron overload may be treated as described herein. In certain embodiments, the term "focal iron overload" does not include diseases or conditions associated with global iron overload (e.g., global iron overload associated with chronic transfusion therapy, hereditary hemochromatosis, etc.). The treatment of focal iron overload may be systemic or local administration of an effective amount of a compound of Formula (I).

The term "reactive oxygen species" or "ROS" refers to molecules or ions formed by the incomplete reduction of oxygen. Reactive oxygen species include superoxide anion $(O_2.^-)$, peroxides such as hydrogen peroxide $(H_2O_2)$, hydroxyl radical (HO.), and hypochlorous acid (HClO). These molecules are typically chemically reactive. Reactive oxygen species may be formed by any number of mechanisms (e.g. enzymatically, by ionizing radiation, by reaction oxygen with a metal). In certain embodiments, the reactive oxygen species are formed by the reduction of oxygen by an iron ion such as $Fe^{+2}$.

The term "closed head injury" refers to any injury to the head that does not penetrate the skull. Closed head injuries may result from falls, blasts, accidents including vehicular accidents, and assaults. Closed head injuries can lead to hemorrhage or brain swelling, which can result in increased intracranial pressure, which can in turn lead to permanent brain damage or even death. Various types of closed head injury include concussions, brain contusions, diffuse axonal injury, and hematomas.

The term "tautomer" refers to a particular isomer of a compound in which a hydrogen and double bond have changed position with respect to the other atoms of the molecule. For a pair of tautomers to exist there must be a mechanism for interconversion. Examples of tautomers include keto-enol forms, imine-enamine forms, amide-imino alcohol forms, amidine-aminidine forms, nitroso-oxime forms, thio ketone-enethiol forms, N-nitroso-hydroxyazo forms, nitro-aci-nitro forms, lactam-lactim forms, keteneynol forms, enamine-enamine forms, and pyridione-hydroxypyridine forms.

(HO)-DADFT-norPE (III-A) in plasma at various time points after a 300 μmol/kg subcutaneous (sc) dose of each compound in rats.

Figure 4:
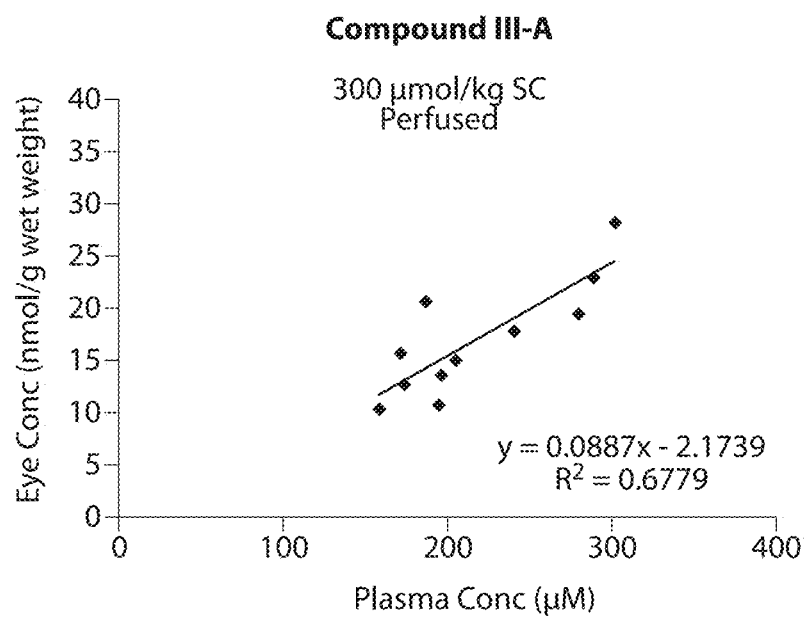

FIG. 4 shows the correlation between plasma concentration and concentration in the eye for (S)-4'-(HO)-DADFT-norPE (III-A) administered 300 μmol/kg subcutaneously (SC) in perfused rats.

Figure 5:
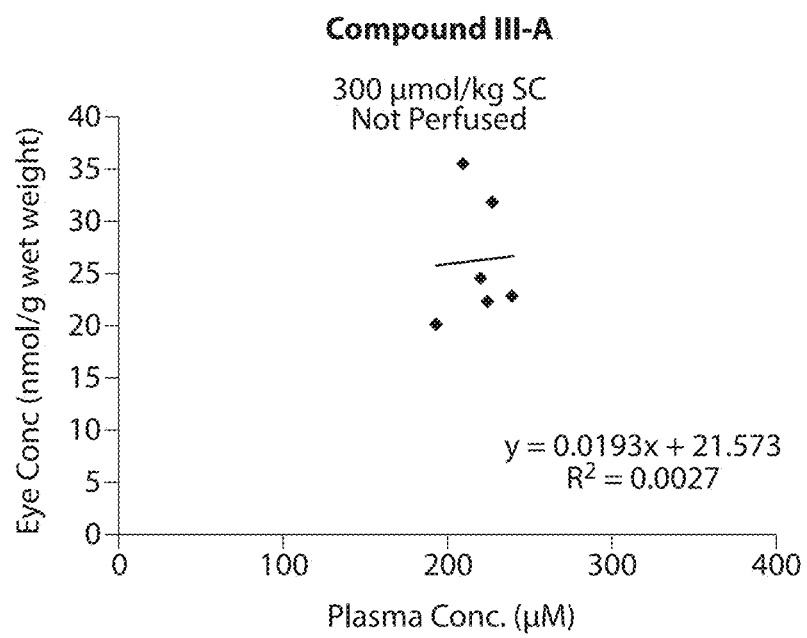

FIG. 5 shows the correlation between plasma concentration and concentration in the eye for (S)-4'-(HO)-DADFT-norPE (III-A) administered 300 μmol/kg subcutaneously (SC) in non-perfused rats.

DETAILED DESCRIPTION OF CERTAIN EMBODIMENTS OF THE INVENTION

Various desferrithiocin analogs have been described for use in the treatment of global iron overload resulting from transfusion therapy, high-iron diet, acute iron ingestion, or malabsorption. Such analogs have now been discovered to be useful in treating or preventing diseases and conditions associated with focal iron overload, where the local concentration of iron in a particular tissue or organ contributes to the pathological process. For instance, the unmanaged $Fe^{+2}$ ions in a tissue or organ may result in the production of hydroxyl radicals or other reactive oxygen species that lead to tissue or cell damage. Therefore, desferrithiocin analogs of Formula (I), particularly those with a polyether moiety at the 4'-position of the phenyl ring, are expected to be useful in the treatment of macular degeneration, closed head injury, reperfusion injury, and stroke. Without wishing to be bound by any particular theory, the compounds of Formula (I) are thought to chelate iron and prevent it from participating in the generation of reactive oxygen species. The compounds of Formula (I) may also act as free radical scavenger thereby limiting the damage of reactive oxygen species or other radicals. The invention, therefore, provides methods of treating and preventing disease and conditions associated with focal iron overload, as well as pharmaceutical compositions and kits useful in the inventive methods.

Useful Compounds

Desferrithiocin analogs of Formula (I) are expected to be useful in preventing and treating diseases and conditions associated with iron overload, particularly focal iron overload. Such analogs have been previously described in International PCT Applications, PCT/US2006/010945, filed Mar. 22, 2006, WO2006/017626, and PCT/US2010/002336, filed Aug. 25, 2010, published as WO2011/028255; and U.S. patent application U.S. Ser. No. 11/973,001, filed Oct. 4, 2007, published as US2008/0214630; each of which is incorporated herein by reference. Compounds with a poly ether moiety at the 4'-position of the phenyl ring are expected to be particularly useful in the methods and compositions of the present invention.

In certain embodiments, compounds useful in the present invention are of Formula (I):

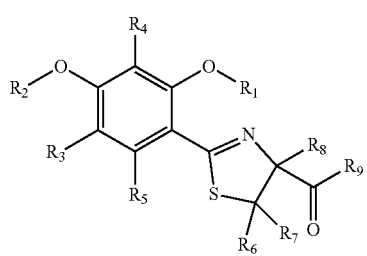

(I)

wherein:
$R_1$ is hydrogen, alkyl, or acyl;
$R_2$ is hydrogen, alkyl, or $-[(CH_2)_n-O]_x-[(CH_2)_n-O]_y-R'$;
$R_3$, $R_4$, and $R_5$ are each independently hydrogen, alkyl, arylalkyl, or $-OR_{10}$;
$R_6$, $R_7$, and $R_8$ are each independently hydrogen, halogen, alkyl, or $-OR_{12}$;
$R_9$ is $-OR_{11}$ or $-SR_{11}$;
$R_{10}$ is hydrogen, alkyl, or acyl;
$R_{11}$ is hydrogen or alkyl;
$R_{12}$ is hydrogen or alkyl;
R' is alkyl;
each occurrence of n is independently an integer from 1 to 8, inclusive;
x is an integer from 1 to 8, inclusive; and
y is an integer from 0 to 8, inclusive;
or a pharmaceutically acceptable salt, tautomer, solvate, hydrate, or polymorph thereof.

In compounds of Formula (I), $R^1$ is hydrogen, alkyl, or acyl. In certain embodiments, $R^1$ is hydrogen. In certain embodiments, $R^1$ is $C_1$-$C_6$ alkyl. In certain embodiments, $R^1$ is methyl. In certain embodiments, $R^1$ is ethyl. In certain embodiments, $R^1$ is propyl. In certain embodiments, $R^1$ is acyl. In certain embodiments, $R^1$ is acetyl.

In compounds of Formula (I), $R_2$ is hydrogen, alkyl, or $-[(CH_2)_n-O]_x-[(CH_2)_n-O]_y-R'$. In certain embodiments, $R_2$ is hydrogen. In certain embodiments, $R_2$ is $C_1$-$C_6$ alkyl. In certain embodiments, $R_2$ is methyl. In certain embodiments, $R_2$ is ethyl. In certain embodiments, $R_2$ is propyl. In certain embodiments, $R_2$ is $-[(CH_2)_n-O]_x-[(CH_2)_n-O]_y-R'$. In certain embodiments, $R_2$ is $-[(CH_2)_2-O]-CH_3$. In certain embodiments, $R_2$ is $-[(CH_2)_2-O]_2-CH_3$. In certain embodiments, $R_2$ is $-[(CH_2)_2-O]_3-CH_3$. In certain embodiments, $R_2$ is $-[(CH_2)_2-O]_4-CH_3$. In certain embodiments, $R_2$ is $-[(CH_2)_2-O]_5-CH_3$.

In compounds of Formula (I), n is an integer from 1 to 8, inclusive. In certain embodiments, n is 2. In certain embodiments, n is 3. In certain embodiments, n is 4. In certain embodiments, n is 5.

In compounds of Formula (I), x is an integer from 1 to 8, inclusive. In certain embodiments, x is 1. In certain embodiments, x is 2. In certain embodiments, x is 3. In certain embodiments, x is 4. In certain embodiments, x is 5.

In compounds of Formula (I), y is an integer from 0 to 8, inclusive. In certain embodiments, y is 0. In certain embodiments, y is 1. In certain embodiments, y is 2. In certain embodiments, y is 3. In certain embodiments, y is 4. In certain embodiments, y is 5.

In compounds of Formula (I), R' is alkyl. In certain embodiments, R' is $C_1$-$C_6$ alkyl. In certain embodiments, R' is methyl. In certain embodiments, R' is ethyl. In certain embodiments, R' is propyl.

In compounds of Formula (I), $R_3$ is each independently hydrogen, alkyl, arylalkyl, or $-OR_{10}$. In certain embodiments, $R_3$ is hydrogen. In certain embodiments, $R_3$ is $C_1$-$C_6$ alkyl. In certain embodiments, $R_3$ is methyl. In certain embodiments, $R_3$ is ethyl. In certain embodiments, $R_3$ is propyl. In certain embodiments, $R_3$ is $-OH$. In certain embodiments, $R_3$ is $-OCH_3$.

In compounds of Formula (I), $R_4$ is each independently hydrogen, alkyl, arylalkyl, or $-OR_{10}$. In certain embodiments, $R_4$ is hydrogen. In certain embodiments, $R_4$ is $C_1$-$C_6$ alkyl. In certain embodiments, $R_4$ is methyl. In certain embodiments, $R_4$ is ethyl. In certain embodiments, $R_4$ is propyl. In certain embodiments, $R_4$ is $-OH$. In certain embodiments, $R_4$ is $-OCH_3$.

In compounds of Formula (I), $R_5$ is each independently hydrogen, alkyl, arylalkyl, or —$OR_{10}$. In certain embodiments, $R_5$ is hydrogen. In certain embodiments, $R_5$ is $C_1$-$C_6$ alkyl. In certain embodiments, $R_5$ is methyl. In certain embodiments, $R_5$ is ethyl. In certain embodiments, $R_5$ is propyl. In certain embodiments, $R_5$ is —OH. In certain embodiments, $R_5$ is —$OCH_3$.

In certain embodiments, $R_3$, $R_4$, and $R_5$ are all hydrogen. In certain embodiments, at least one of $R_3$, $R_4$, and $R_5$ is hydrogen. In certain embodiments, at least two of $R_3$, $R_4$, and $R_5$ are hydrogen.

In compounds of Formula (I), $R_6$ is hydrogen, halogen, alkyl, or —$OR_{12}$. In certain embodiments, $R_6$ is hydrogen. In certain embodiments, $R_6$ is halogen. In certain embodiments, $R_6$ is $C_1$-$C_6$ alkyl. In certain embodiments, $R_6$ is methyl. In certain embodiments, $R_6$ is ethyl. In certain embodiments, $R_6$ is propyl. In certain embodiments, $R_6$ is —OH. In certain embodiments, $R_6$ is —$OCH_3$.

In compounds of Formula (I), $R_7$ is hydrogen, halogen, alkyl, or —$OR_{12}$. In certain embodiments, $R_7$ is hydrogen. In certain embodiments, $R_7$ is halogen. In certain embodiments, $R_7$ is $C_1$-$C_6$ alkyl. In certain embodiments, $R_7$ is methyl. In certain embodiments, $R_7$ is ethyl. In certain embodiments, $R_7$ is propyl. In certain embodiments, $R_7$ is —OH. In certain embodiments, $R_7$ is —$OCH_3$.

In certain embodiments, both $R_6$ and $R_7$ are hydrogen. In certain embodiments, at least one of $R_6$ and $R_7$ is hydrogen.

In compounds of Formula (I), $R_8$ is hydrogen, halogen, alkyl, or —$OR_{12}$. In certain embodiments, $R_8$ is hydrogen. In certain embodiments, $R_8$ is halogen. In certain embodiments, $R_8$ is $C_1$-$C_6$ alkyl. In certain embodiments, $R_8$ is methyl. In certain embodiments, $R_8$ is ethyl. In certain embodiments, $R_8$ is propyl. In certain embodiments, $R_8$ is —OH. In certain embodiments, $R_8$ is —$OCH_3$.

In compounds of Formula (I), $R_9$ is —$OR_{11}$ or —$SR_{11}$, wherein $R_{11}$ is hydrogen or alkyl. In certain embodiments, $R_9$ is —OH. In certain embodiments, $R_9$ is —$OCH_3$. In certain embodiments, $R_9$ is —$OCH_2CH_3$. In certain embodiments, $R_9$ is —$OCH(CH_3)_2$. In certain embodiments, $R_9$ is —$SCH_3$. In certain embodiments, $R_9$ is —$SCH_2CH_3$. In certain embodiments, $R_9$ is —$SCH_2CH_2CH_3$. In certain embodiments, $R_9$ is —$SCH(CH_3)_2$. In certain embodiments, $R_9$ is —$SCH_2CH(CH_3)_2$. In certain embodiments, $R_{11}$ is hydrogen. In certain embodiments, $R_{11}$ is $C_1$-$C_6$ alkyl.

In certain embodiments, $R_6$ is hydrogen, $R_7$ is hydrogen, and $R_8$ is methyl.

In certain embodiments, $R_3$ is hydrogen, $R_4$ is hydrogen, $R_5$ is hydrogen, $R_6$ is hydrogen, $R_7$ is hydrogen, and $R_8$ is methyl.

In certain embodiments, $R_1$ is hydrogen, $R_3$ is hydrogen, $R_4$ is hydrogen, $R_5$ is hydrogen, $R_6$ is hydrogen, $R_7$ is hydrogen, and $R_8$ is methyl.

In certain embodiments, $R_1$ is hydrogen, $R_3$ is hydrogen, $R_4$ is hydrogen, $R_5$ is hydrogen, $R_6$ is hydrogen, $R_7$ is hydrogen, $R_8$ is methyl, and $R_9$ is —OH.

The compounds of Formula (I) may be provided in various salts forms. In certain embodiments, when $R_9$ is —OH, the compound may be provided as a carboxylate salt with a positively charged counterion. In certain embodiments, the counterion is betaine, choline hydroxide, diethanolamine, diethylamine, ethanolamine, hydroxyethylmorpholine, 4-(2-hydroxyethyl morpholine), 1-(2-hydroxyethyl pyrrolidine), 1-(2-hydroxyethyl)-piperidine, 1,2-EDSA, HCl, $H_2SO_4$, MSA, p-TSA, hydroxyethyl pyrrolidine, imidazone, lysine (e.g., L-lysine), arginine (e.g., L-arginine), histidine (e.g., L-histidine) N-methyl-D-glucamine (NMG), N, N'-dibenzyl-ethylenediamine, N, N'-diethyl-ethanolamine, triethanolamine, tromethamine, calcium (e.g., $Ca(OH)_2$), magnesium (e.g., $Mg(OH)_2$, magnesium acetate), potassium (e.g., KOH, potassium 2-ethylhexanoate), sodium (e.g., NaOH, sodium acetate, sodium 2-ethylhexanoate), zinc (e.g., $Zn(OH)_2$, zinc acetate), $Zn(OH)_2/Mg(OH)_2$, EDA, or piperazine. In certain embodiments, the counterion is lysine. In certain embodiments, the counterion is N-methyl-D-glucamine (NMG). In certain embodiments, the counterion is tromethamine. In certain embodiments, the counterion is calcium. In certain embodiments, the counterion is magnesium. In certain embodiments, the counterion is potassium. In certain embodiments, the counterion is sodium, In certain embodiments, the counterion is zinc. In certain embodiments, the counterion is piperazine. In certain embodiments, the counterion is $MgOH^+$. In certain embodiments, the counterion is $ZnOH^+$.

In certain embodiments, a polymorph of a salt of a compound of Formula (I) is provided. In certain embodiments, a polymorph of a magnesium salt of a compound of Formula (I) is provided. In certain embodiments, a polymorph of a $MgOH^+$ salt of a compound of Formula (I) is provided. In certain embodiments, a polymorph of a salt of a carboxylate compound of Formula (I), wherein $R_9$ is —OH, is provided. In certain embodiments, a polymorph of a magnesium salt of a carboxylate compound of Formula (I), wherein $R_9$ is —OH, is provided. In certain embodiments, a polymorph of a $MgOH^+$ salt of a carboxylate compound of Formula (I), wherein $R_9$ is —OH, is provided.

In certain embodiments, the compound of Formula (I) is of Formula (III):

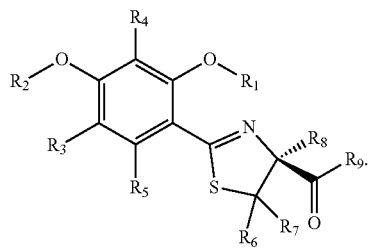

(III)

In certain embodiments, the compound of Formula I) is of Formula (III-A):

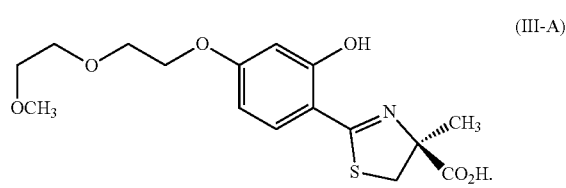 [SMILES: COCCOCCOc1ccc(C2=N[C@@](C)(C(=O)O)CS2)c(O)c1]

(III-A)

In certain embodiments, a salt of a compound of Formula (III-A) is provided. In certain embodiments, a magnesium hydroxide salt of Formula (III-A) is provided as shown in Formula (III-A'):

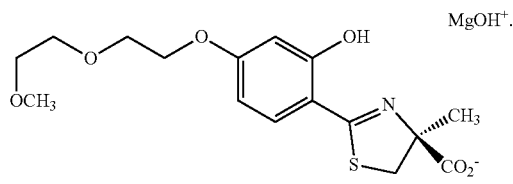
(III-A')

In certain embodiments, the compound of Formula (I) is of Formula (III-B):

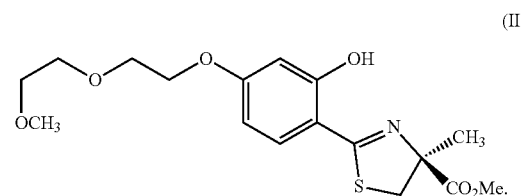
(III-B)

In certain embodiments, the compound of Formula (I) is of Formula (III-C):

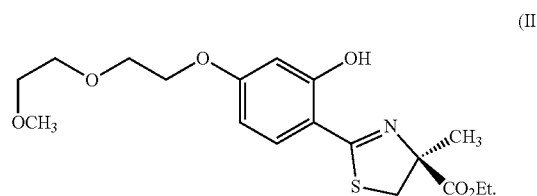
(III-C)

In certain embodiments, the compound of Formula (I) is of Formula (IV-A):

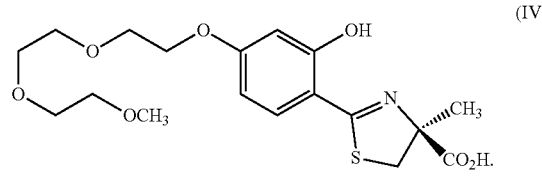
(IV-A)

In certain embodiments, a salt of a compound of Formula (IV-A) is provided. In certain embodiments, a magnesium hydroxide salt of Formula (IV-A) is provided as shown in Formula (IV-A'):

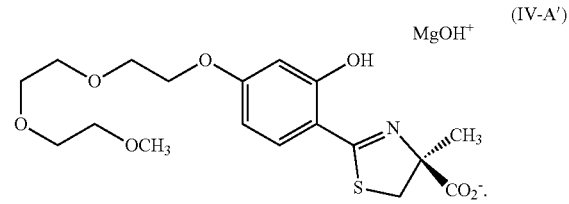
(IV-A')

In certain embodiments, the compound of Formula (I) is of Formula (IV-B):

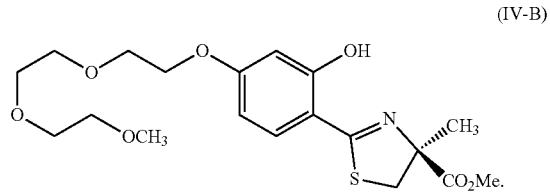 [SMILES: COCCOCCOCCOc1ccc(C2=N[C@@](C)(C(=O)OC)CS2)c(O)c1]
(IV-B)

In certain embodiments, the compound of Formula (I) is of Formula (IV-C):

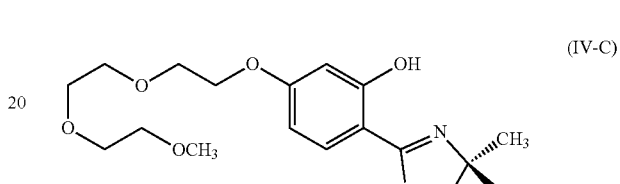
(IV-C)

In certain embodiments, the compound of Formula (I) is of Formula (V-A):

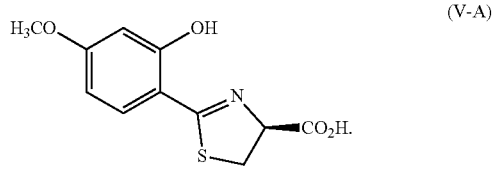
(V-A)

In certain embodiments, the compound of Formula (I) is of Formula (V-B):

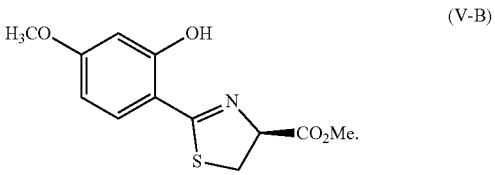
(V-B)

In certain embodiments, the compound of Formula (I) is of Formula (V-C):

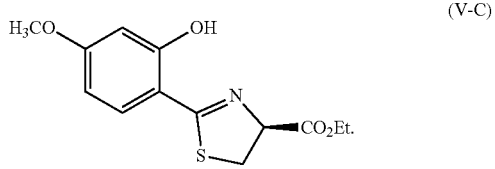 [SMILES: CCOC(=O)[C@H]1CSC(c2ccc(OC)cc2O)=N1]
(V-C)

Treatment of Macular Degeneration

In one aspect, the invention provides methods and pharmaceutical compositions for the treatment of macular degeneration. Without wishing to be bound by a particular theory, the compounds of Formula (I) are able to get into the eye as shown in FIGS. 4 and 5. The compounds of Formula (I) are then able to chelate and remove iron from the eye thereby preventing $Fe^{+2}$ from forming and generating reactive oxygen species. The local accumulation of iron is thought to contribute to macular degeneration. Therefore, the removal of iron from the eye (including the retina) can prevent and treat macular degeneration.

In the treatment of macular degeneration, the compound of Formula (I) or a pharmaceutical composition thereof may be administered systemically or ocularly. In certain embodiments, the compound or composition is administered orally. In other embodiments, the compound or composition is administered to the eye using eyedrops or an ointment suitable for ocular administration.

The subject being treated for macular degeneration may be any type of animal. In certain embodiments, the animal is a mammal. In certain embodiments, the animal is a human. In certain embodiments, the animal is a domesticated animal (e.g., dog, cat, pig, cow). In certain embodiments, the animal is a research animal (e.g., mice, rat, dog, primate).

The exact amount of the compound of Formula (I) required to treat or prevent macular degeneration will vary from subject to subject, depending on the species, age, and general condition of the subject, the particular agent being administered, its mode of administration, and the like. The compound is preferably formulated in a dosage unit form for ease of administration and uniformity of dosage. It will be understood, however, that the total daily dosage will be decided by a physician within the scope of sound medical judgment. The specific therapeutically effective dose level for any particular subject will depend upon a variety of factors including the severity of the macular degeneration; the specific compound be administered; the age, body weight, general health, sex, and diet of the subject; the time of administration, route of administration, and rate of excretion of the particular compound being administered; the duration of the treatment; drugs used in combination or coincidental with the particular compound being administered; and like factors well known in the medical arts. In certain embodiments, the daily dosage of the compound of Formula (I) for the treatment of macular degeneration in a subject may range from 0.01 mg/kg to 200 mg/kg per unit dosage. In certain embodiments, the daily dosage ranges from 0.1 mg/kg to 100 mg/kg. In certain embodiments, the daily dosage ranges from 0.1 mg/kg to 50 mg/kg. In certain embodiments, the daily dosage ranges from 0.1 mg/kg to 20 mg/kg. In certain embodiments, the daily dosage ranges from 0.1 mg/kg to 10 mg/kg. In certain embodiments, the daily dosage ranges from 0.1 mg/kg to 1 mg/kg. In certain embodiments, the compound or a composition thereof may be administered once a day to multiple times per day. In certain embodiments, a fraction of the daily dose is administered once, twice, three times, or four times daily. In other embodiments, the compound of a composition thereof is administered every other day, every third day, every week, every other week, or every month.

Treatment of Head Injury

The compounds of Formula (I) and pharmaceutical compositions thereof are expected to be useful in the treatment of head injury, particularly those involving bleeding into the brain or other parts of the central nervous system. Without wishing to be bound by any particular theory, the compounds of Formula (I) are thought to chelate the iron from red blood cells the blood resulting from the head injury, thereby preventing iron ions from generating reactive oxygen species. In the case of head injury resulting in bleeding into the central nervous system where the vasculature has been compromised a compound being used may or may not have the ability to cross the blood brain barrier. In certain embodiments, the compound being used to treat a head injury in a subject is able to cross the blood brain barrier. In other embodiments, the compounds is not able to cross the blood brain barrier. Certain compounds of Formula (I) have been found in the CSF after systemic administration (po and sc).

Head injuries come in various forms and results from various causes. In certain embodiments, the injury is an injury to the head that penetrates the skull. In other embodiments, the head injury being treated is a closed head injury, which does penetrate the skull. Closed head injuries results from a variety of causes including accidents including vehicular accidents, falls, and assaults. Types of closed head injuries include concussions, brain contusions, diffuse axonal injury, and hematoma. In certain embodiments, the closed head injury being treated in the present invention include closed head injuries that result in blood outside the blood vessels of the brain. The local accumulation of iron from the bleeding is thought to contribute to after effects of closed head injury. By assisting the clearance of iron from the brain the effects of the bleed are minimized.

In the treatment of closed head injury, the compound of Formula (I) or a pharmaceutical composition thereof may be administered systemically, for example, parenterally or orally. In certain embodiments, the compound or composition is administered orally. In other embodiments, the compound or composition is administered parenterally (e.g., intravenously).

The subject being treated for a head injury may be any type of animal. In certain embodiments, the animal is a mammal. In certain embodiments, the animal is a human. In certain embodiments, the animal is a domesticated animal (e.g., dog, cat, pig, cow). In certain embodiments, the animal is a research animal (e.g., mice, rat, dog, primate).

The exact amount of the compound of Formula (I) required to treat a head injury will vary from subject to subject, depending on the species, age, and general condition of the subject, the particular agent being administered, its mode of administration, and the like. The compound is preferably formulated in a dosage unit form for ease of administration and uniformity of dosage. It will be understood, however, that the total daily dose will be decided by a physician using sound medical judgment. The specific therapeutically effective dose level for any particular subject will depend upon a variety of factors including the severity of the head injury; the specific compound be administered; the age, body weight, general health, sex, and diet of the subject; the time of administration, route of administration, and rate of excretion of the particular compound being administered; the duration of the treatment; drugs used in combination or coincidental with the particular compound being administered; and like factors well known in the medical arts. In certain embodiments, the daily dosage of the compound of Formula (I) for the treatment of a head injury in a subject may range from 0.01 mg/kg to 200 mg/kg per unit dosage. In certain embodiments, the daily dosage ranges from 0.1 mg/kg to 100 mg/kg. In certain embodiments, daily dosage ranges from 0.1 mg/kg to 50 mg/kg. In certain embodiments, the daily dosage ranges from 0.1 mg/kg to 20 mg/kg. In certain embodiments, the daily dosage ranges from 0.1 mg/kg to 10 mg/kg. In certain embodiments, the daily dosage ranges from 0.1 mg/kg to 1 mg/kg. In certain embodiments, the compound or a composition thereof may be administered once a day to multiple times per day. In certain embodiments, a fraction of the daily dose is administered once, twice, three times, or four times daily. In other embodiments, the compound of a composition thereof is administered every other day, every third day, every week, every other week, or every month. In certain embodiments, the inventive treatment is stopped once the head injury is resolved, or it is thought the inventive treatment would no longer be beneficial. In certain embodiments, the treatment is stopped once the bleeding has been resolved in a subject with a head injury.

Treatment of Stroke

The present invention also provides for the treatment of stroke. The inventive treatment typically leads to a better and/or faster recovery from stroke. The stroke being treated may be either a ischemic stroke or a hemorrhagic stroke. In the treatment of an ischemic stroke, a compound of Formula (I) or composition thereof is administered to a subject to prevent or minimize the damage due to reperfusion injury after the blood supply to the affected part of the brain is restore. The compound is thought to prevent the generation of reactive oxygen species by either chelating iron responsible for the generation of such species and/or quenching such radical species when they do occur. In hemorrhagic stroke, the compound is thought to work by similar mechanisms although the sequestering of iron from the blood in the brain is probably the predominate mechanism by which the inventive treatment works. The mechanism of action of the compound of Formula (I) is similar to that in the treatment of head injury.

The compound being used in the treatment may have the ability to cross the blood brain barrier. In certain embodiments, the compound has the ability to cross the blood brain barrier. In other embodiments, the compound does not have the ability to cross the blood brain barrier. In certain embodiments, when the subject has been diagnosed with an ischemic stroke, the compound used in the treatment can pass through the blood brain barrier.

The present invention may be useful in treating a subject after the subject has been diagnosed with having a stroke, or a subject who is susceptible to having a stroke may be administered a compound of Formula (I) or composition thereof to prevent or minimize the stroke's effects. In certain embodiments, the compound is administered as quickly as possible after a subject has been diagnosed with having a stroke. In certain embodiments, the compound is administered to the subject while the stroke is still occurring. In certain embodiments, the compound or a composition thereof is administered to a subject who has a history of strokes or is susceptible to having a stroke because of the subject's underlying medical condition. The compound or composition thereof may be administered once or multiple times in the treatment of stroke.

In the treatment of stroke the compound of Formula (I) or a pharmaceutical composition thereof may be administered systemically, for example, parenterally or orally. In certain embodiments, the compound or composition is administered orally. In other embodiments, the compound or composition is administered parenterally (e.g., intravenously).

The subject being treated for stroke may be any type of animal. In certain embodiments, the animal is a mammal. In certain embodiments, the animal is a human. In certain embodiments, the animal is a domesticated animal (e.g., dog, cat, pig, cow). In certain embodiments, the animal is a research animal (e.g., mice, rat, dog, primate).

The exact amount of the compound of Formula (I) required to treat a stroke will vary from subject to subject, depending on the species, age, and general condition of the subject, the particular agent being administered, its mode of administration, and the like. The compound is preferably formulated in a dosage unit form for ease of administration and uniformity of dosage. It will be understood, however, that the total daily dose will be decided by a physician using sound medical judgment. The specific therapeutically effective dose level for any particular subject will depend upon a variety of factors including the severity of the stroke; the specific compound be administered; the age, body weight, general health, sex, and diet of the subject; the time of administration, route of administration, and rate of excretion of the particular compound being administered; the duration of the treatment; drugs used in combination or coincidental with the particular compound being administered; and like factors well known in the medical arts. In certain embodiments, the daily dosage of the compound of Formula (I) for the treatment of a stroke in a subject may range from 0.01 mg/kg to 200 mg/kg per unit dosage. In certain embodiments, the daily dosage ranges from 0.1 mg/kg to 100 mg/kg. In certain embodiments, the daily dosage ranges from 0.1 mg/kg to 50 mg/kg. In certain embodiments, the daily dosage ranges from 0.1 mg/kg to 20 mg/kg. In certain embodiments, the daily dosage ranges from 0.1 mg/kg to 10 mg/kg. In certain embodiments, the daily dosage ranges from 0.1 mg/kg to 1 mg/kg. In certain embodiments, the compound or a composition thereof may be administered once a day to multiple times per day. In certain embodiments, a fraction of the daily dose is administered once, twice, three times, or four times daily. In other embodiments, the compound or a composition thereof is administered every other day, every third day, every week, every other week, or every month. Typically the compound or composition thereof is not administered after it is no longer thought to be beneficial, for example, when all the bleeding has been cleared in a hemorrhagic stroke.

Treatment of Inflammatory Bowel Disease

Figure 1:
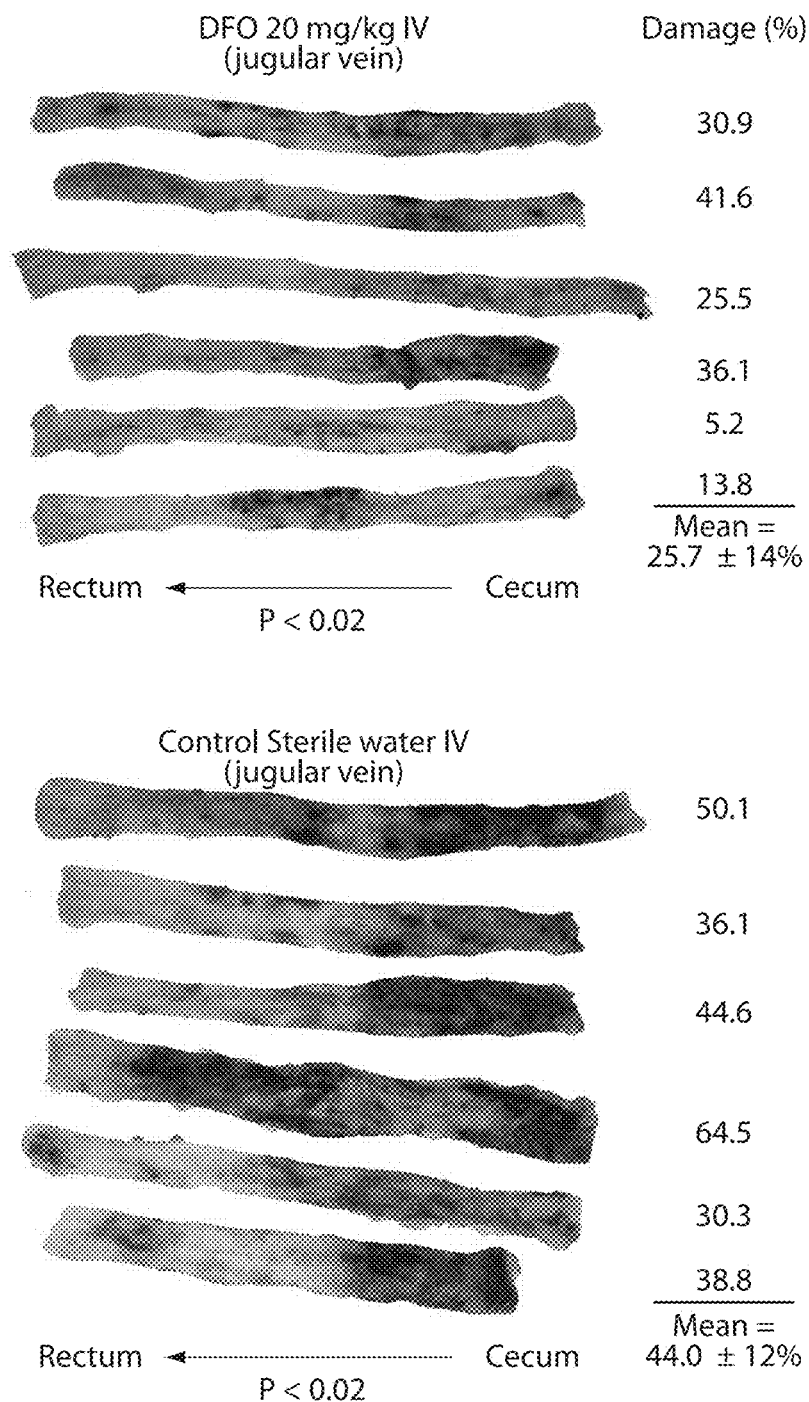
FIG. 1 shows representative colons from rats treated with desferrioxamine (DFO) (20 mg/kg) IV and sterile water (control) 30 minutes before the 4% acetic acid. Each colon is positioned such that the cecum is on the right and the rectum is on the left.

Reactive oxygen species have been implicated in the pathogenesis of inflammatory bowel disease (IBD). Grisham et al., "Neutophil-mediated mucosal injury. Role of reactive oxygen metabolites" *Dig. Dis. Sci.* 33:6S-15S, 1988; All-gayer "Clinical relevance of oxygen radicals in inflammatory bowel disease-facts and fashion" *Klin. Wochenschr.* 69:1001-1003, 1991; Ymamada et al. "Role of neutrophil-derived oxidants in the pathogenesis of intestinal inflammation" *Klin. Wocheschr.* 69:988-944, 1991; Babbs, "Oxygen radicals in ulcerative colitis" *Free Radic. Biol. Med.* 13:169-181, 1992. The present invention provides for the treatment of IBD. DFO, an iron chelator, has been discovered to prevent acetic acid-induced colitis in rats, an animal model of IBD. See FIG. 1 and Example 2. See, also, Bergeron et al., "Prevention of Acetic Acid-Induced Colitis by Desferrithiocin Analogs in a Rat Model" *Digestive Diseases and Sciences,* 48(2):399-407, February 2003. The compounds used in the inventive treatment are thought to prevent or eliminate the generation of reactive oxygen species or other longer-lived, more stable radicals that may be responsible for the tissue damage and inflammation seen in subjects with IBD. Another possible mechanism of action of the compounds useful in the invention is the chelation of metal, such as iron, which may contribute to the generation of reactive oxygen species, such as hydroxyl radicals and hydrogen peroxide, that cause cell damage.

The present invention may be useful in treating a subject diagnosed with IBD. The treatment may be used to treat the subject long term or may be used to treat a subject with a fare up of IBD. A therapeutically effective amount of a compound of Formula (I) or composition thereof is administered to a subject in need thereof to treat IBD. In certain embodiments, treatment with a compound of Formula (I) leads to reduced levels of reactive oxygen species in the intestines, specifically the intestinal mucosa. The compound or composition thereof may be administered to a subject once or multiple times in the treatment of IBD.

In the treatment of IBD, the compound of Formula (I) or a pharmaceutical composition thereof may be administered systemically, for example, parenterally or orally. In certain embodiments, the compound or composition is administered orally. In other embodiments, the compound or composition is administered parenterally (e.g., intravenously). In certain embodiments, the compound or a composition is administered rectally.

The subject being treated for IBD may be any type of animal. In certain embodiments, the animal is a mammal. In certain embodiments, the animal is a human. In certain embodiments, the animal is a domesticated animal (e.g., dog, cat, pig, cow). In certain embodiments, the animal is a research animal (e.g., mice, rat, dog, primate). In certain embodiments, the animal is used in animal model of IBD (e.g., acetic acid-induced colitis in rats; see Fedorak et al., "Misoprostol provides a colonic mucosal protective effect during acetic acid-induced colitis in rats" *Gastroenterology* 98:615-625, 1990; MacPherson et al., "Experimental production of diffuse colitis in rats" *Digestion* 17:135-150, 1978).

The exact amount of the compound of Formula (I) required to treat IBD will vary from subject to subject, depending on the species, age, and general condition of the subject, the particular agent being administered, its mode of administration, and the like. The compound is preferably formulated in a dosage unit form for ease of administration and uniformity of dosage. The total daily dose will be decided by a physician using sound medical judgment. The specific therapeutically effective dose level for any particular subject will depend upon a variety of factors including the severity of IBD; the specific compound be administered; the age, body weight, general health, sex, and diet of the subject; the time of administration, route of administration, and rate of excretion of the particular compound being administered; the duration of the treatment; drugs used in combination or coincidental with the particular compound being administered; and like factors well known in the medical arts. In certain embodiments, the daily dosage of the compound of Formula (I) for the prevention or treatment of reperfusion injury in a subject may range from 0.01 mg/kg to 200 mg/kg per unit dosage. In certain embodiments, the daily dosage ranges from 0.1 mg/kg to 100 mg/kg. In certain embodiments, the daily dosage ranges from 0.1 mg/kg to 50 mg/kg. In certain embodiments, the daily dosage ranges from 0.1 mg/kg to 20 mg/kg. In certain embodiments, the daily dosage ranges from 0.1 mg/kg to 10 mg/kg. In certain embodiments, the daily dosage ranges from 0.1 mg/kg to 1 mg/kg. In certain embodiments, the compound or a composition thereof may be administered once a day to multiple times per day. In certain embodiments, a fraction of the daily dose is administered once, twice, three times, or four times daily. In other embodiments, the compound or a composition thereof is administered every other day, every third day, every week, every other week, or every month.

Treatment of Reperfusion Injury

The present invention also provides for the treatment of reperfusion injury. Reperfusion injury may occur in any area of the body where the blood supply has been compromised. In certain embodiments, the reperfusion injury being treated occurs in the heart. In other embodiments, the reperfusion injury occurs in the brain, for example, as discussed above in the context of a stroke The inventive treatment minimizes reperfusion injury once the blood supply to the affects organ or tissue is restored. In the treatment or prevention of reperfusion injury, a compound of Formula (I) or composition thereof is administered to a subject who is suffering from ischemia of a tissue or organ. The compound of Formula (I) is thought to prevent the generation of reactive oxygen species by either chelating iron responsible for the generation of such species and/or quenching such radical species when they do occur.

The present invention may be useful in treating a subject after the subject has been diagnosed with ischemia of a particular organ or tissue. A therapeutically effective amount of a compound of Formula (I) or composition thereof is administered to a subject to prevent or minimize reperfusion injury. In certain embodiments, the compound is administered as quickly as possible after a subject has been diagnosed with ischemia. In certain embodiments, the compound is administered to the subject at risk of ischemia. In certain embodiments, the compound or a composition thereof is administered to a subject who is about to undergo a procedure that may lead to ischemia of an organ or tissue (e.g., cardiac surgery). In certain embodiments, the compound or a composition thereof is used to prevent reperfusion injury in a transplanted organ. In certain embodiments, the compound or composition thereof is used to perfuse an isolated organ being prepared for donation. The compound or composition thereof may be administered to a subject once or multiple times in the treatment of reperfusion injury.

In the prevention or treatment of reperfusion injury, the compound of Formula (I) or a pharmaceutical composition thereof may be administered systemically, for example, parenterally or orally. In certain embodiments, the compound or composition is administered orally. In other embodiments, the compound or composition is administered parenterally (e.g., intravenously). In certain embodiments, the compound or a composition is administered locally to the organ or tissue suffering from ischemia.

The subject being treated for reperfusion injury may be any type of animal. In certain embodiments, the animal is a mammal. In certain embodiments, the animal is a human. In certain embodiments, the animal is a domesticated animal (e.g., dog, cat, pig, cow). In certain embodiments, the animal is a research animal (e.g., mice, rat, dog, primate).

The exact amount of the compound of Formula (I) required to prevent or treat reperfusion injury will vary from subject to subject, depending on the species, age, and general condition of the subject, the particular agent being administered, its mode of administration, and the like. The compound is preferably formulated in a dosage unit form for ease of administration and uniformity of dosage. It will be understood, however, that the total daily dose will be decided by a physician using sound medical judgment. The specific therapeutically effective dose level for any particular subject will depend upon a variety of factors including the severity of the reperfusion injury; the specific compound be administered; the age, body weight, general health, sex, and diet of the subject; the time of administration, route of administration, and rate of excretion of the particular compound being administered; the duration of the treatment; drugs used in combination or coincidental with the particular compound being administered; and like factors well known in the medical arts. In certain embodiments, the daily dosage of the compound of Formula (I) for the prevention or treatment of reperfusion injury in a subject may range from 0.01 mg/kg to 200 mg/kg per unit dosage. In certain embodiments, the daily dosage ranges from 0.1 mg/kg to 100 mg/kg. In certain embodiments, the daily dosage ranges from 0.1 mg/kg to 50 mg/kg. In certain embodiments, the daily dosage ranges from 0.1 mg/kg to 20 mg/kg. In certain embodiments, the daily dosage ranges from 0.1 mg/kg to 10 mg/kg. In certain embodiments, the daily dosage ranges from 0.1 mg/kg to 1 mg/kg. In certain embodiments, the compound or a composition thereof may be administered once a day to multiple times per day. In other embodiments, the compound or a composition thereof is administered every other day, every third day, every week, every other week, or every month. Typically the compound or composition thereof is not administered after it is no longer thought to be beneficial, for example, when the risk of reperfusion injury is over.

Pharmaceutical Compositions

The present invention also provides pharmaceutical compositions of Formula (I) for the treatment of macular degeneration, closed head injury, stroke, IBD, and reperfusion injury. After formulation with an appropriate pharmaceutically acceptable excipient in a desired dosage, the pharmaceutical compositions of this invention can be administered to humans and other animals orally, rectally, parenterally, intracisternally, intraperitoneally, topically, bucally, ocularly, or the like, depending on the disease or condition being treated. In certain embodiments, an agent of the invention may be administered orally or parenterally at dosage levels sufficient to deliver from about 0.001 mg/kg to about 200 mg/kg, about 0.001 mg/kg to about 100 mg/kg, about 0.01 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). In certain embodiments, a compound of Formula (I) is administered at a dose that is below the dose at which the agent causes non-specific effects. In certain embodiments, a compound of Formula (I) is administered at a dose that does not cause generalized immunosuppression in a subject.

Liquid dosage forms for oral and parenteral administration include, but are not limited to, pharmaceutically acceptable emulsions, microemulsions, solutions, suspensions, syrups, and elixirs. In addition to the active agents, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can also include adjuvants such as wetting agents, emulsifying and suspending agents, sweetening, flavoring, and perfuming agents. In certain embodiments for parenteral administration, agents of the invention are mixed with solubilizing agents such CREMOPHOR EL® (polyethoxylated castor oil), alcohols, oils, modified oils, glycols, polysorbates, cyclodextrins, polymers, and combinations thereof.

Injectable preparations, for example, sterile injectable aqueous or oleaginous suspensions, may be formulated according to the known art using suitable dispersing or wetting agents and suspending agents. Sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the compounds of this invention with suitable non-irritating excipients or carriers such as cocoa butter, polyethylene glycol, or a suppository wax which are solid at ambient temperature but liquid at body temperature and therefore melt in the rectum or vaginal cavity and release the active agent.

Solid dosage forms for oral administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active agents can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Formulations suitable for topical administration include liquid or semi-liquid preparations such as liniments, lotions, gels, applicants, oil-in-water or water-in-oil emulsions such as creams, ointments, or pastes; or solutions or suspensions such as drops. Formulations for topical administration to the skin surface can be prepared by dispersing the drug with a dermatologically acceptable carrier such as a lotion, cream, ointment, or soap. Useful carriers are capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used. Ophthalmic formulation, ear drops, and eye drops are also contemplated as being within the scope of this invention. Additionally, the present invention contemplates the use of transdermal patches, which have the added advantage of providing controlled delivery of an agent to the body. Such dosage forms can be made by dissolving or dispensing the agent in the proper medium. Absorption enhancers can also be used to increase the flux of the agent across the skin. The rate can be controlled by either providing a rate controlling membrane or by dispersing the agent in a polymer matrix or gel.

Additionally, the carrier for a topical formulation can be in the form of a hydroalcoholic system (e.g., liquids and gels), an anhydrous oil or silicone based system, or an emulsion system, including, but not limited to, oil-in-water, water-in-oil, water-in-oil-in-water, and oil-in-water-in-silicone emulsions. The emulsions can cover a broad range of consistencies including thin lotions (which can also be suitable for spray or aerosol delivery), creamy lotions, light creams, heavy creams, and the like. The emulsions can also include microemulsion systems. Other suitable topical carriers include anhydrous solids and semisolids (such as gels and sticks); and aqueous based mousse systems.

It will also be appreciated that the compounds of Formula (I) and pharmaceutical compositions thereof can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder, or they may achieve different effects (e.g., control of any adverse effects).

In still another aspect, the present invention also provides a pharmaceutical pack or kit comprising one or more containers filled with one or more of the ingredients of the pharmaceutical compositions of the present invention, and in certain embodiments, includes an additional approved therapeutic agent for use as a combination therapy. Optionally associated with such container(s) can be a notice in the form prescribed by a governmental agency regulating the manufacture, use, or sale of pharmaceutical products, which notice reflects approval by the agency of manufacture, use, or sale for human administration.

EXAMPLES

In order that the invention described herein may be more fully understood, the following examples are set forth. It should be understood that these examples are for illustrative purposes only and are not to be construed as limiting this invention in any manner.

Example 1. Preparation of Sample Solutions

Synthesis of the Desferrithiocin (DFT) Analogs

The desferrithiocin (DFT) analogs and salts thereof useful in the present invention can be prepared from readily available starting materials using methods known in the art. For example, (S)-4'-(HO)-DADFT-norPE (III-A) and (S)-4'-(HO)-DADFT-PE (IV-A) may be synthesized using methods described in International PCT Applications, PCT/US2006/010945, filed Mar. 22, 2006, published as WO 2006/107626, PCT/US2010/002336, filed Aug. 25, 2010, published as WO2011/028255, and U.S. patent application U.S. Ser. No. 11/973,001, filed Oct. 4, 2007, each of which is incorporated herein by reference in its entirety.

Preparation of Sample Solutions Containing Monosodium Salts of the DFT Analogs

The DFT analogs useful in the inventive methods were converted from the free acid form to the monosodium salt form. Water followed by one equivalent of sodium hydroxide was added to the DFT analog as a free acid. The resulting slurry was vortexed or sonicated until the DFT analog went into solution. More water was added, and the solution was vortexed or sonicated again. The formed yellow solution, having a pH about 7, was used as a sample solution in the following Examples. It is preferred that a fresh sample solution of the DFT analog is made shortly before the solution is used in an assay.

Example 2. Prevention of Acetic Acid-Induced Colitis by Desferrithiocin Analogs in a Rat Model Induction of colitis. Male Sprague-Dawley rats (250-350 g) were anesthetized with sodium pentobarbital, 55 mg/kg intraperitoneally. The abdomen was shaved and prepared for surgery. A midline incision was made, and the cecum and proximal colon were exteriorized. A reversible suture was placed at the junction of the cecum and proximal colon. The colon was rinsed with saline (10 ml), and the fluid and intestinal contents were gently expressed out the rectum. A gum-based rectal plug was inserted. The compound of interest, or distilled water in the control animals (2 ml), was injected intracolonically just distal to the ligature. The cecum and proximal colon were returned to the abdominal cavity; the compound was allowed to remain in the gut for 30 min. Then, the cecum and proximal colon were exteriorized again. The rectal plug was removed, and the drug was gently expressed out of the colon. Acetic acid (4%, 2 ml) was injected into the proximal colon over a 15- to 20-sec time period. The acid was allowed to remain in the gut until 1 min had passed (ie, 40-45 sec after the end of the acid administration). The no-acid control rats received distilled water (2 ml), which was administered in the same manner as was the acetic acid. Air (10 ml) was then injected into the proximal colon to expel the acid or water. The cecal/proximal colon ligature was removed, the gut was returned to the abdominal cavity, and the incisions were closed. The animals were allowed to recover overnight and were killed 24 hr later. The entire length of the colon was removed and assessed for damage both densitometrically and biochemically.

Quantitation of acetic acid-induced colitis. Gross damage was quantitated using Photoshop-based image analysis (version 5.0, Adobe Systems, Mountain View, Calif., USA) on an Apple iMac computer. The Magic Wand tool in the Select menu of Photoshop was used to place the cursor on an area of obvious damage. The tolerance level of the Magic Wand tool was set at 30. The damaged areas were automatically selected by using the Similar command in the Select menu. Then, the Eyedropper tool was used to determine the range of the damage in the highlighted areas. Individual colon images were copied to a blank Photoshop page. The MagicWand tool, with a tolerance set to 100, was used to select all of the pixels in the colon sample. Then, the Histogram tool, which generates a graph in which each vertical line represents the number of pixels associated with a brightness level, was selected in the Image menu. The Red channel was then selected; the darker (damaged areas) appear on the left side of the histogram and the lighter (normal) areas are on the right side. The cursor was then placed on the histogram, the color range determined in an earlier step was selected, and the number of pixels encompassing that range and the percent damage were quantitated automatically.

Collection of Chelator Tissue Distribution Samples from Rodents. Male Sprague-Dawley rats (250-350 g) were given the chelators orally at a dose of 300 µmol/kg. At times 0.5, 1, 2, 4 and 8 h after dosing (n=3) rats per time point, the animals were euthanized by exposure to $CO_2$ gas. Blood was obtained via cardiac puncture into vacutainers containing sodium citrate. The blood was centrifuged, and the plasma was separated for analysis. The liver, heart, pancreas, and kidneys were removed from the animals and frozen.

Figure 2:
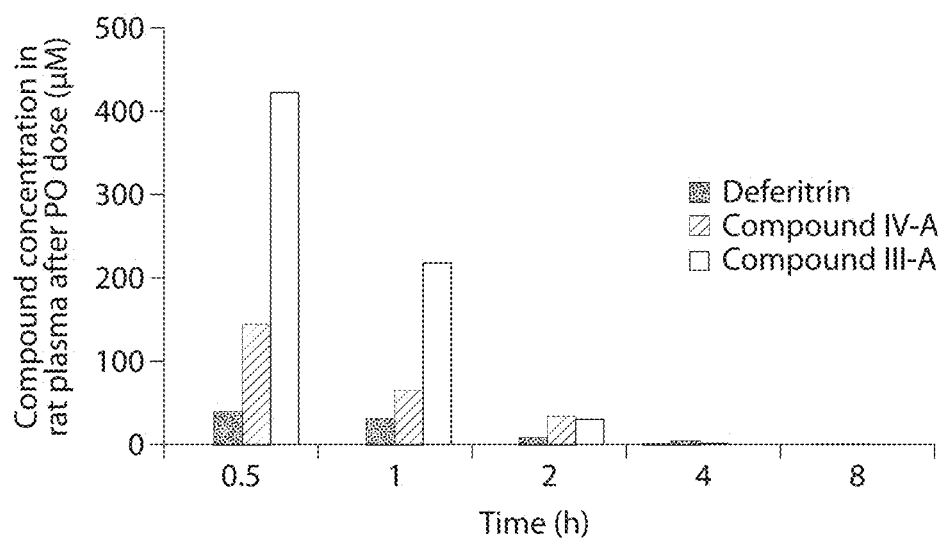
FIG. 2 is a bar graph showing the concentration of Deferitrin, (S)-4'-(HO)-DADFT-PE (IV-A), and (S)-4'-(HO)-DADFT-norPE (III-A) in plasma at various time points after a 300 μmol/kg oral (po) dose of each compound in rats.
Figure 3:
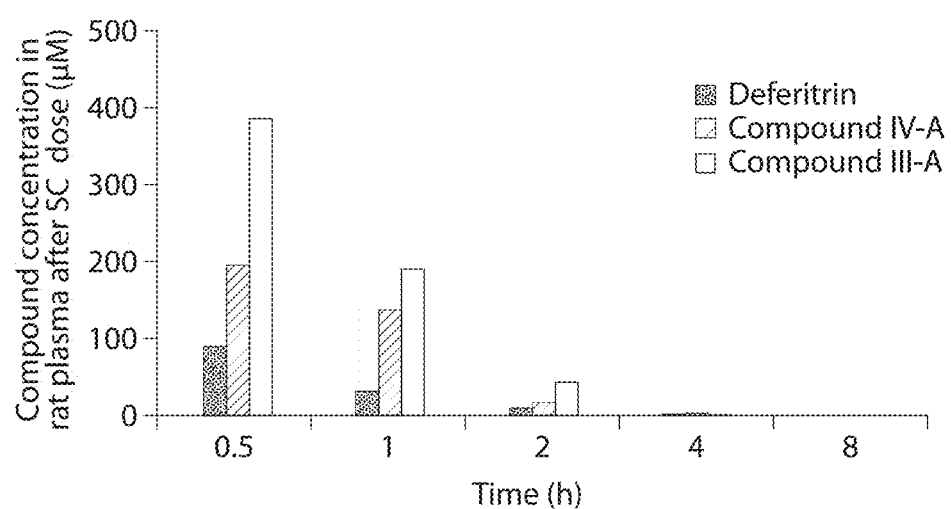
FIG. 3 is a bar graph showing the concentration of Deferitrin, (S)-4'-(HO)-DADFT-PE (IV-A), and (S)-4'-

Example 3. Concentration of DFT Analogs in Rat Plasma after PO (Oral) and SC (Subcutaneous) Dose Male Sprague-Dawley rats (250-350 g) were given a single s.c. injection or an oral dose of the monosodium salt of deferitin, (S)-4'-(HO)-DADFT-norPE (III-A), or (S)-4'-(HO)-DADFT-PE (IV-A) at a dose of 300 µmol/kg. At times 0.5, 1, 2, 4, and 8 hours (n=3) rats per time point, the animals were euthanized by exposure to C02 gas. Blood was obtained via cardiac puncture into vacutainers containing sodium citrate. The blood was centrifuged, and the plasma was separated for analysis. See FIGS. 2 and 3.

Example 4. Concentration of DFT Analogs in Rat Plasma and Cerebrospinal Fluid after PO (Oral) or SC (Subcutaneous) Dose Adult male Sprague-Dawley rats (450-500 g) were used. The rats were not fasted. A sample solution of a monosodium salt of (S)-4'-(HO)-DADFT-norPE (III-A) or (S)-4'-(HO)-DADFT-PE (IV-A) was administered to the rats at an oral or subcutaneous dose of 300 µmol/kg. Concentrations of the DFT analogs in the plasma and cerebrospinal fluid of the rats were measured at 0.5 hour, 1 hour, 2 hours, 4 hours, and 8 hours post administration.

Example 5. Concentration of DFT Analogs in Rat Plasma and Eyes after Subcutaneous Dose Rats were not Perfused Rats were anesthetized with ketamine/xylazine about 50 minutes after dosing. Blood of the rats was collected via cardiac puncture into vacutainer tubes containing buffered sodium citrate one hour post dose. The rats' eyes were removed. Any extraneous tissue was trimmed and discarded. The eyes were frozen. The entire eye was then processed and assessed for the concentration of the DFT analog. The whole blood was centrifuged, and the plasma was separated and frozen until the concentration of the DFT analog was determined.

Rats were Perfused with Saline

Rats were anesthetized with ketamine/xylazine about 50 minutes after dosing. Blood of the rats was collected via cardiac puncture into vacutainer tubes containing buffered sodium citrate one hour post dose. The rats' abdomen and thorax were opened, and a portion of the sternum/ribs was removed. A 19-gauge needle was inserted into the left ventricle of the rats, and the right atrium was cut. About 100 ml of saline was perfused transcardially for five minutes. The perfusion was stopped, and the rats' eyes were removed. Any extraneous tissue was trimmed and discarded. The eyes were frozen. The entire eye was then processed and assessed for the concentration of the DFT analog. The whole blood was centrifuged, and the plasma was separated and frozen until the concentration of the DFT analog was determined.

TABLE 1

Concentration of DFT analogs in the plasma and cerebrospinal fluid of rats treated with the DFT analogs at a PO dose of 300 µmol/kg

| DFT analog | $LogP_{app}$ | Time (h) | Concentration in plasma (µM) | Concentration in cerebrospinal fluid (µM) |
|---|---|---|---|---|
| IV-A | −1.10 | 0.5 | 142 ± 57 | 2.14 ± 1.01 |
| | | 1 | 64 ± 7 | trace |
| | | 2 | 32 ± 20 | trace |
| | | 4 | 2 ± 0.5 | trace |
| | | 8 | trace | trace |
| III-A | −0.89 | 0.5 | 424 ± 60 | 8.07 ± 3.09 |
| | | 1 | 219 ± 19 | 5.70 ± 2.74 |
| | | 2 | 30 ± 5 | 2.32 (only 1 out 3 animals showed anything) |
| | | 4 | 2 ± 0.4 | 0 ± 0 |
| | | 8 | trace | 0 ± 0 |

TABLE 2

Concentration of DFT analogs in the plasma and eyes of rats treated with the DFT analogs at a SC dose of 300 μmol/kg*

| DFT analog | $LogP_{app}$ | Non-perfused | | Perfused with saline | |
|---|---|---|---|---|---|
| | | Concentration in plasma (μM) | Concentration in the eye (nmol/g wet weight of the eye) | Concentration in plasma (μM) | Concentration in the eye (nmol/g wet weight of the eye) |
| III-A | −0.89 | 218 ± 16 | 25.8 ± 6.0 | 218 ± 51 | 17.2 ± 5.5 |
| V-A | −0.89 | 701 ± 32 | 37.8 ± 4.3 | 663 ± 42 | 29.7 ± 4.3 |

*The rats were anesthetized about 50 minutes after dose. The non-perfused rates were killed by exposure to $CO_2$ one hour post dose. The remaining rats were perfused transcardially one hour post dose with about 100 ml of saline for 5 minutes.

The foregoing written specification is considered to be sufficient to enable one skilled in the art to practice the present invention. The present invention is not to be limited in scope by the examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the claims. The advantages and objects of the present invention are not necessarily encompassed by each embodiment of the invention.

All publications, patent applications, and patents mentioned herein are hereby incorporated by reference in their entirety for disclosure of the teachings relevant to the present invention, as if each individual publication, patent application, or patent was specifically and individually indicated to be incorporated by reference. In case of the present specification and a document incorporated by reference including conflicting disclosure, the present specification shall control.

What is claimed is:

1. A method of treating macular degeneration in a subject comprising administering to the subject a therapeutically effective amount of a compound of Formula (III-A):

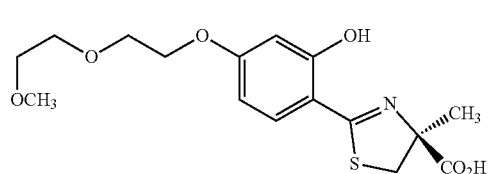

(III-A)

or a pharmaceutically acceptable salt thereof.

2. The method of claim 1, wherein the compound is of Formula (III-A):

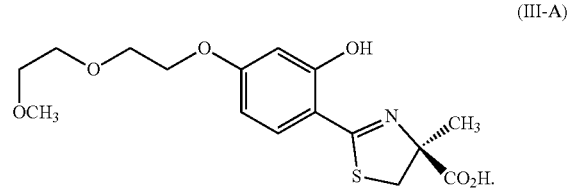 [SMILES: COCCOCCOc1ccc(C2=N[C@@](C)(C(=O)O)CS2)c(O)c1]

(III-A)

3. The method of claim 1, wherein the compound is a pharmaceutically acceptable alkali or alkaline earth metal salt of the compound of Formula (III-A):

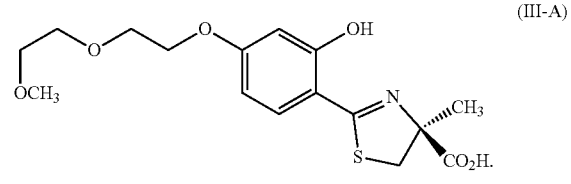 [SMILES: COCCOCCOc1ccc(C2=N[C@@](C)(C(=O)O)CS2)c(O)c1]

(III-A)

4. The method of claim 1, wherein the compound is a sodium, lithium, potassium, calcium or magnesium salt of the compound of Formula (III-A):

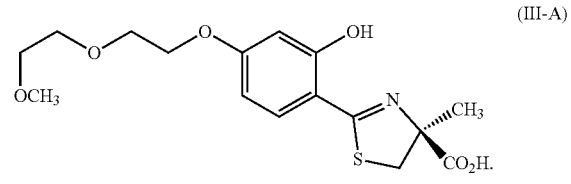 [SMILES: COCCOCCOc1ccc(C2=N[C@@](C)(C(=O)O)CS2)c(O)c1]

(III-A)

5. The method of claim 1, wherein the compound is a sodium salt of the compound of Formula (III-A):

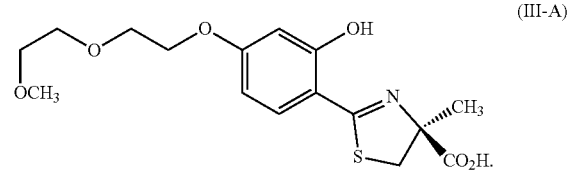 [SMILES: COCCOCCOc1ccc(C2=N[C@@](C)(C(=O)O)CS2)c(O)c1]

(III-A)

6. The method of claim 1, wherein the compound is a magnesium hydroxide salt of the compound of Formula (III-A) as shown in Formula (III-A'):

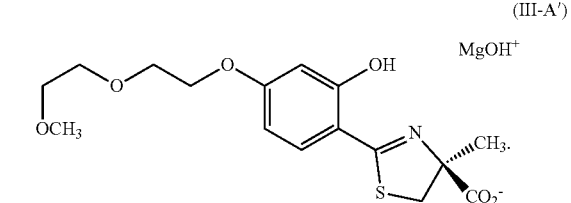

(III-A')

* * * * *